(12) United States Patent  
Buttermann

(10) Patent No.: US 10,709,480 B2
(45) Date of Patent: Jul. 14, 2020

(54) ADJUSTABLE SCREW-CLAMP ORTHOPEDIC APPARATUS

(71) Applicant: DYNAMIC SPINE, LLC, Mahtomedi, MN (US)

(72) Inventor: Glenn R. Buttermann, Mahtomedi, MN (US)

(73) Assignee: DYNAMIC SPINE, LLC, Mahtomedi, MN (US)

( * ) Notice: Subject to any disclaimer, the term of this patent is extended or adjusted under 35 U.S.C. 154(b) by 285 days.

(21) Appl. No.: 15/300,635

(22) PCT Filed: Apr. 16, 2015

(86) PCT No.: PCT/US2015/026165
§ 371 (c)(1),
(2) Date: Sep. 29, 2016

(87) PCT Pub. No.: WO2015/161071
PCT Pub. Date: Oct. 22, 2015

(65) Prior Publication Data
US 2017/0181772 A1    Jun. 29, 2017

Related U.S. Application Data

(60) Provisional application No. 61/980,265, filed on Apr. 16, 2014.

(51) Int. Cl.
*A61B 17/70* (2006.01)

(52) U.S. Cl.
CPC ...... *A61B 17/7047* (2013.01); *A61B 17/7032* (2013.01); *A61B 17/7056* (2013.01)

(58) Field of Classification Search
CPC ............ A61B 17/7047; A61B 17/7056; A61B 17/707; A61B 17/7064; A61B 17/7065; A61B 17/7062
See application file for complete search history.

(56) References Cited

U.S. PATENT DOCUMENTS 5,395,370 A    3/1995  Muller et al.
5,415,659 A *  5/1995  Lee ..................... A61B 17/7007
                                                      24/569

(Continued)

FOREIGN PATENT DOCUMENTS

WO    WO-2005037115 A1 *  4/2005   ......... A61B 17/7055
WO    WO-2009/156875 A2    12/2009

(Continued)

OTHER PUBLICATIONS

English translation of specification of WO-2005037115-A1 (Year: 2005).*

(Continued)

*Primary Examiner* — Amy R Sipp
(74) *Attorney, Agent, or Firm* — Foley & Lardner LLP

(57) ABSTRACT

A screw-clamp apparatus is disclosed that may include a first clamp component comprising a first attachment end and at least one hook on a first hook end, a second clamp component comprising a second attachment end and at least one hook on a second hook end, a bone-screw hole located in one of the first clamp component and the second clamp component, a bone screw configured to be inserted through the bone-screw hole and to be inserted into bone, a first spacer-receiver located on one of the first clamp component and the second clamp component, and a length adjusting mechanism configured to adjust a longitudinal length of the screw-clamp apparatus. The first attachment end and the second attachment end are configured to attach the first clamp component and the second clamp component together. The first spacer-receiver is configured to secure a spacer.

6 Claims, 36 Drawing Sheets

(56) References Cited

U.S. PATENT DOCUMENTS

| | | | |
|---|---|---|---|
| 6,051,007 | A | 4/2000 | Hogendijk et al. |
| 6,368,320 | B1* | 4/2002 | Le Couedic ....... A61B 17/7049 606/246 |
| 2003/0045876 | A1 | 3/2003 | Stahurski |
| 2003/0114856 | A1* | 6/2003 | Nathanson ......... A61B 17/8009 606/70 |
| 2008/0234733 | A1* | 9/2008 | Scrantz ............. A61B 17/7062 606/246 |
| 2011/0137353 | A1* | 6/2011 | Buttermann ....... A61B 17/7001 606/305 |
| 2012/0095510 | A1 | 4/2012 | Nihalani |
| 2013/0131738 | A1 | 5/2013 | Powell et al. |

FOREIGN PATENT DOCUMENTS

| | | |
|---|---|---|
| WO | WO-2011/004222 A1 | 1/2011 |
| WO | WO-2014/164490 A1 | 10/2014 |

OTHER PUBLICATIONS

Machine English translation of specification of WO-2005037115-A1 (Year: 2005).*

International Search Report in PCT/US2015/026165 dated Sep. 18, 2015, 4 pages.

Written Opinion of the International Searching Authority in PCT/US2015/026165 dated Sep. 18, 2015, 5 pages.

Supplementary European Search Report dated Dec. 1, 2017 in corresponding European Patent Application No. 15 77 9562.6 10 pages.

International Preliminary Report on Patentability and Transmittal received in corresponding International Application No. PCT/US2015/026165 dated Oct. 27, 2016, 7 pages.

* cited by examiner

FIG. 1A
FIG. 1B
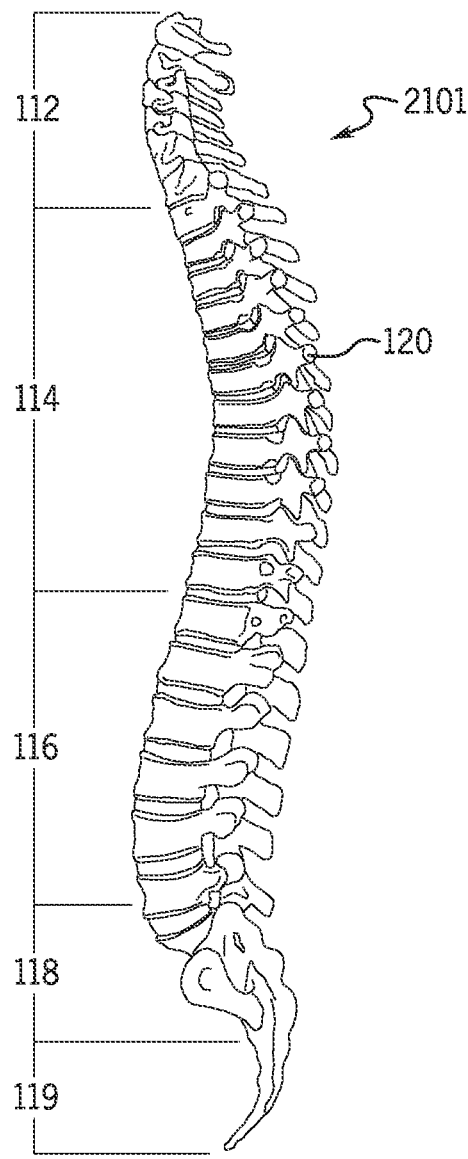
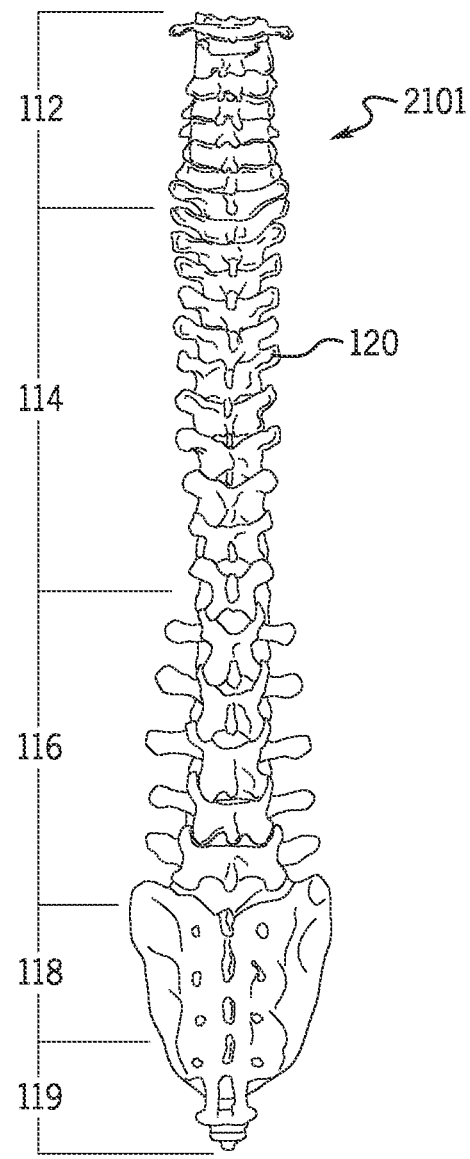

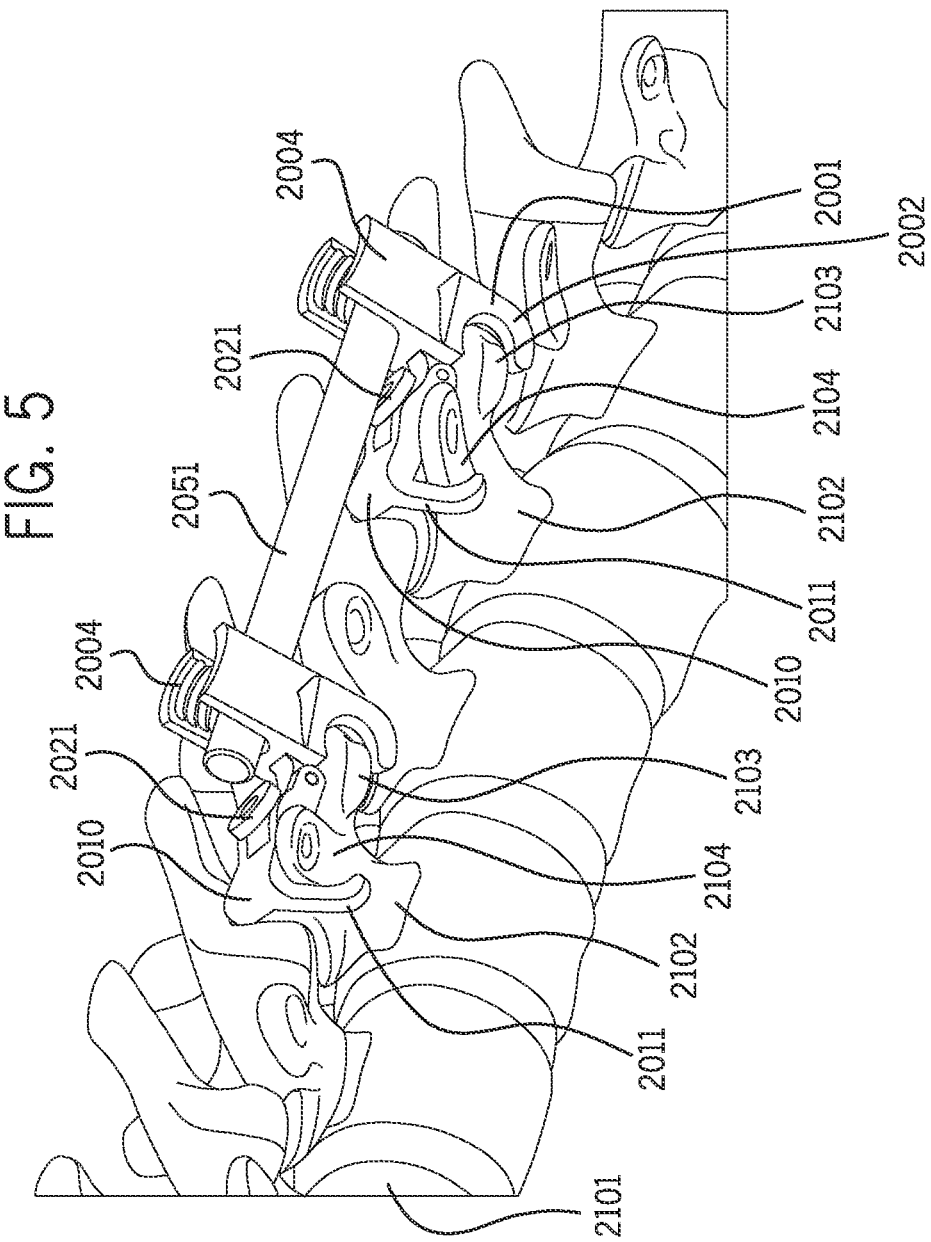

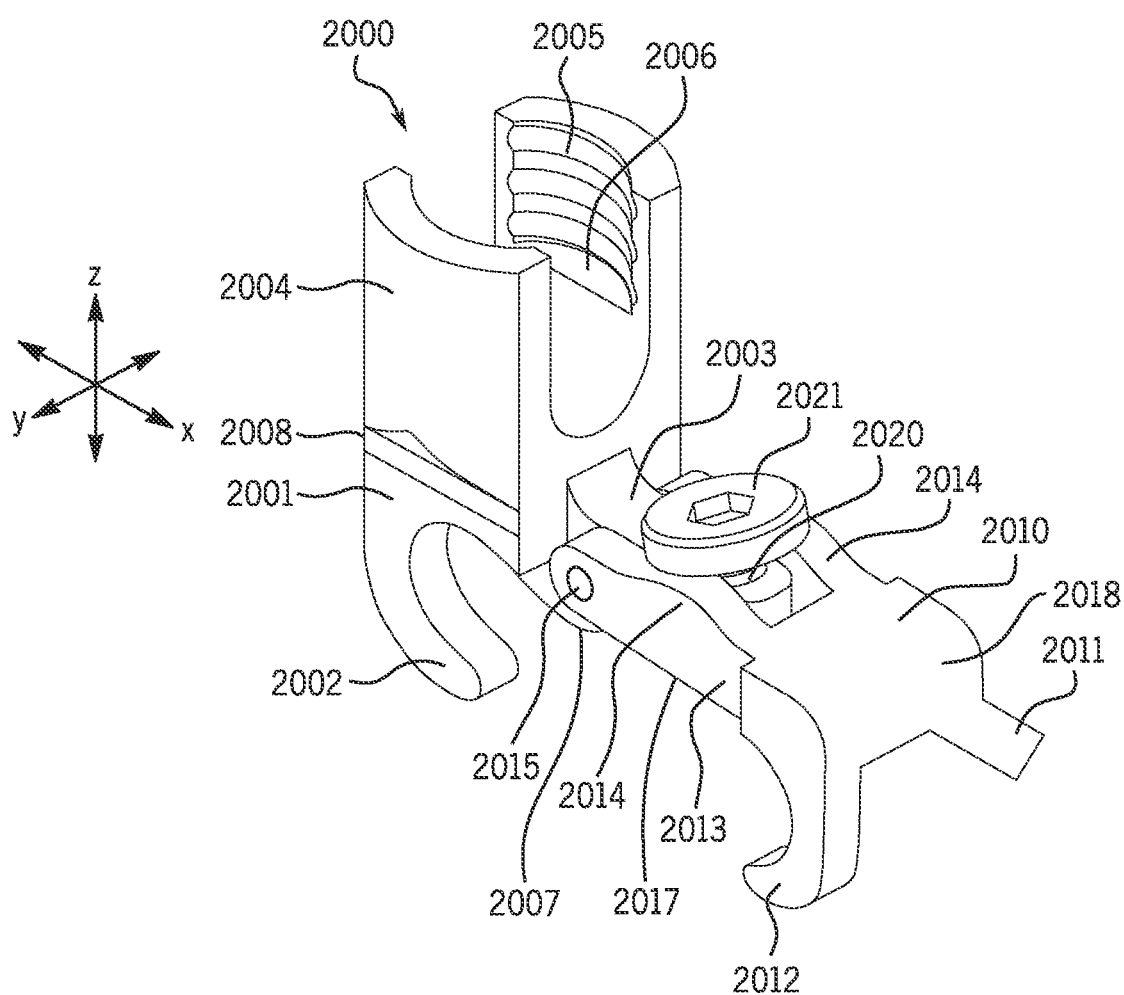

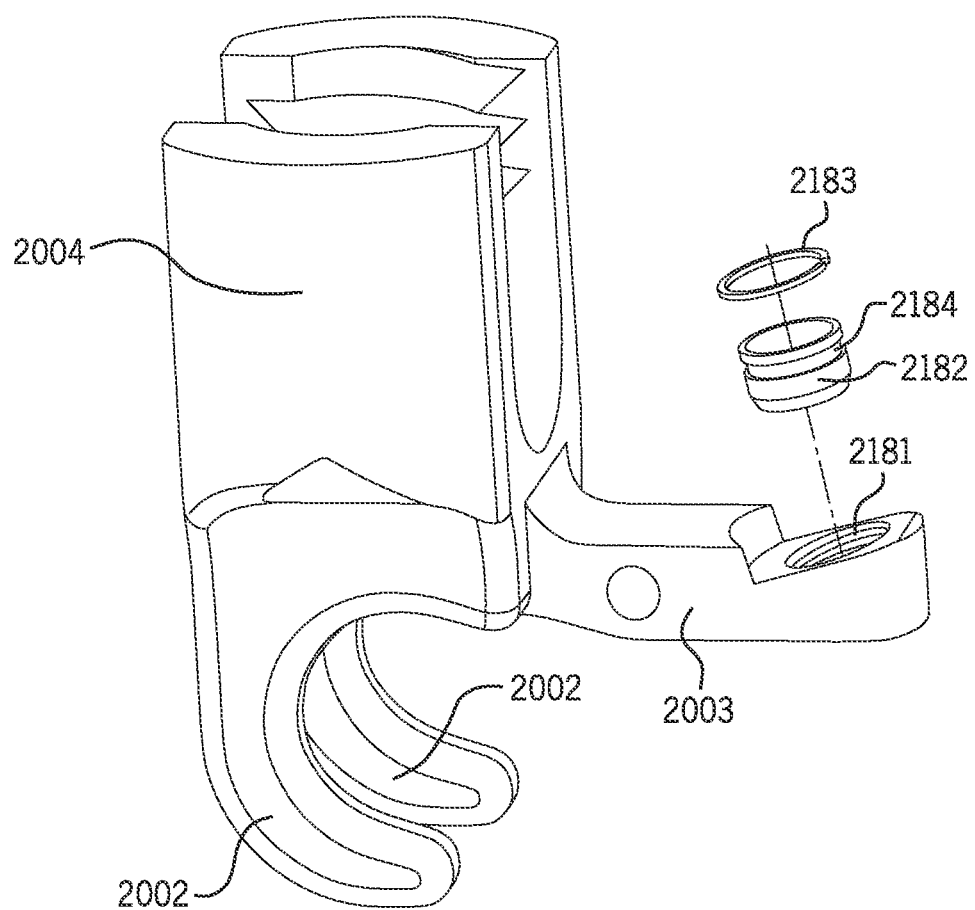

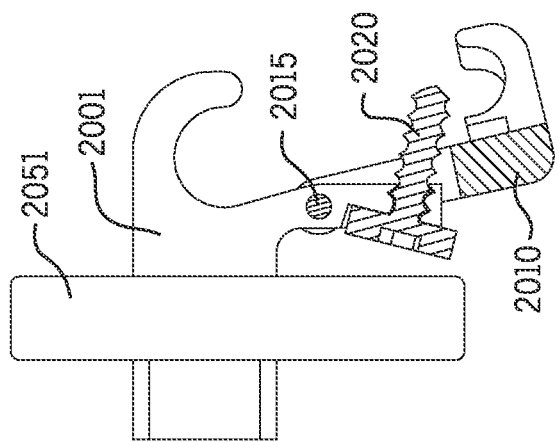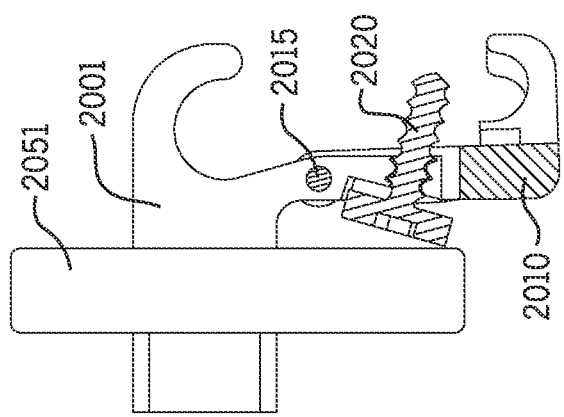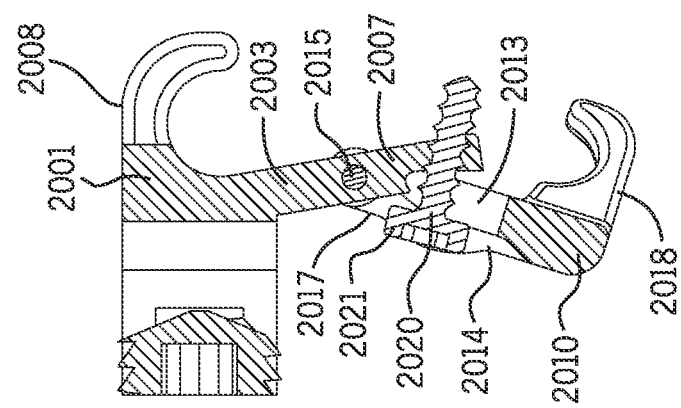

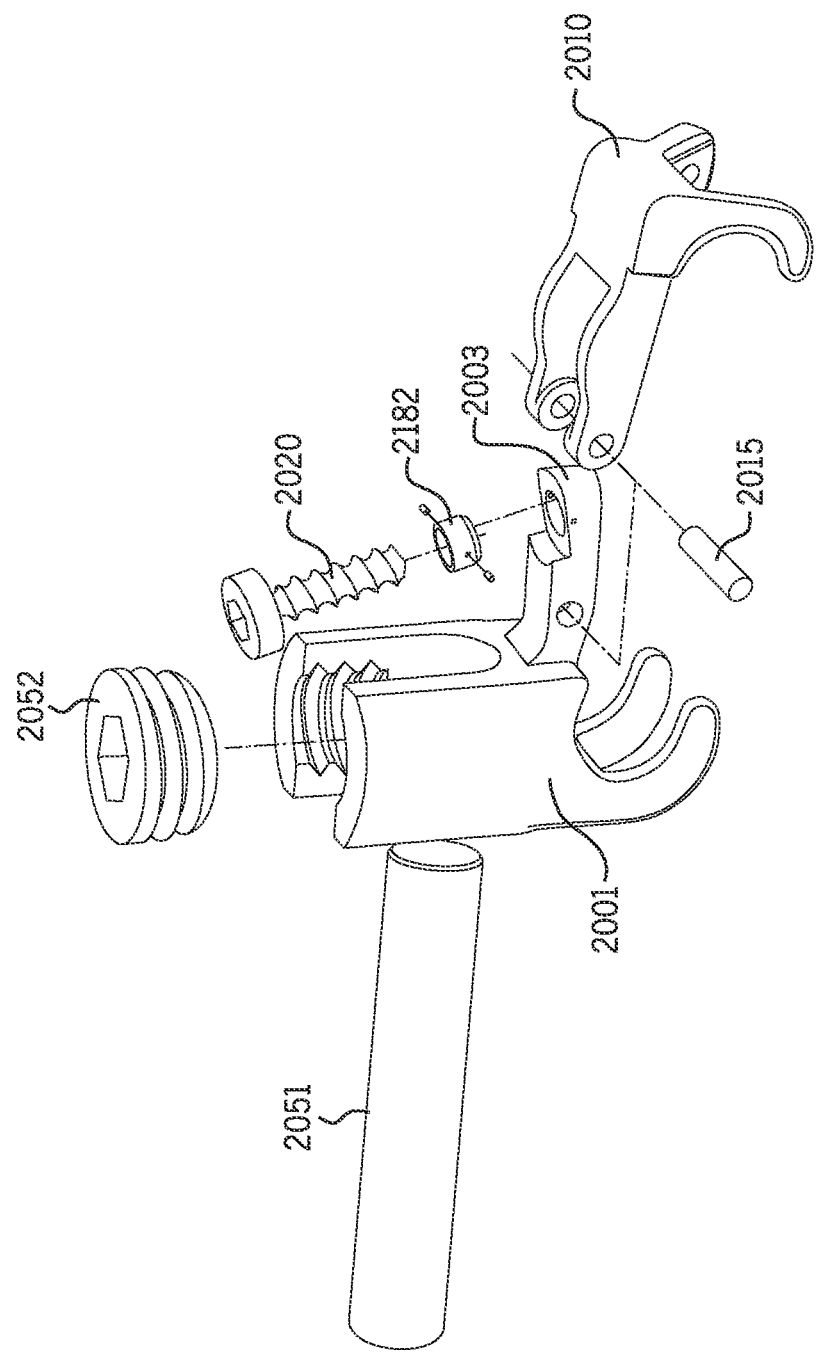

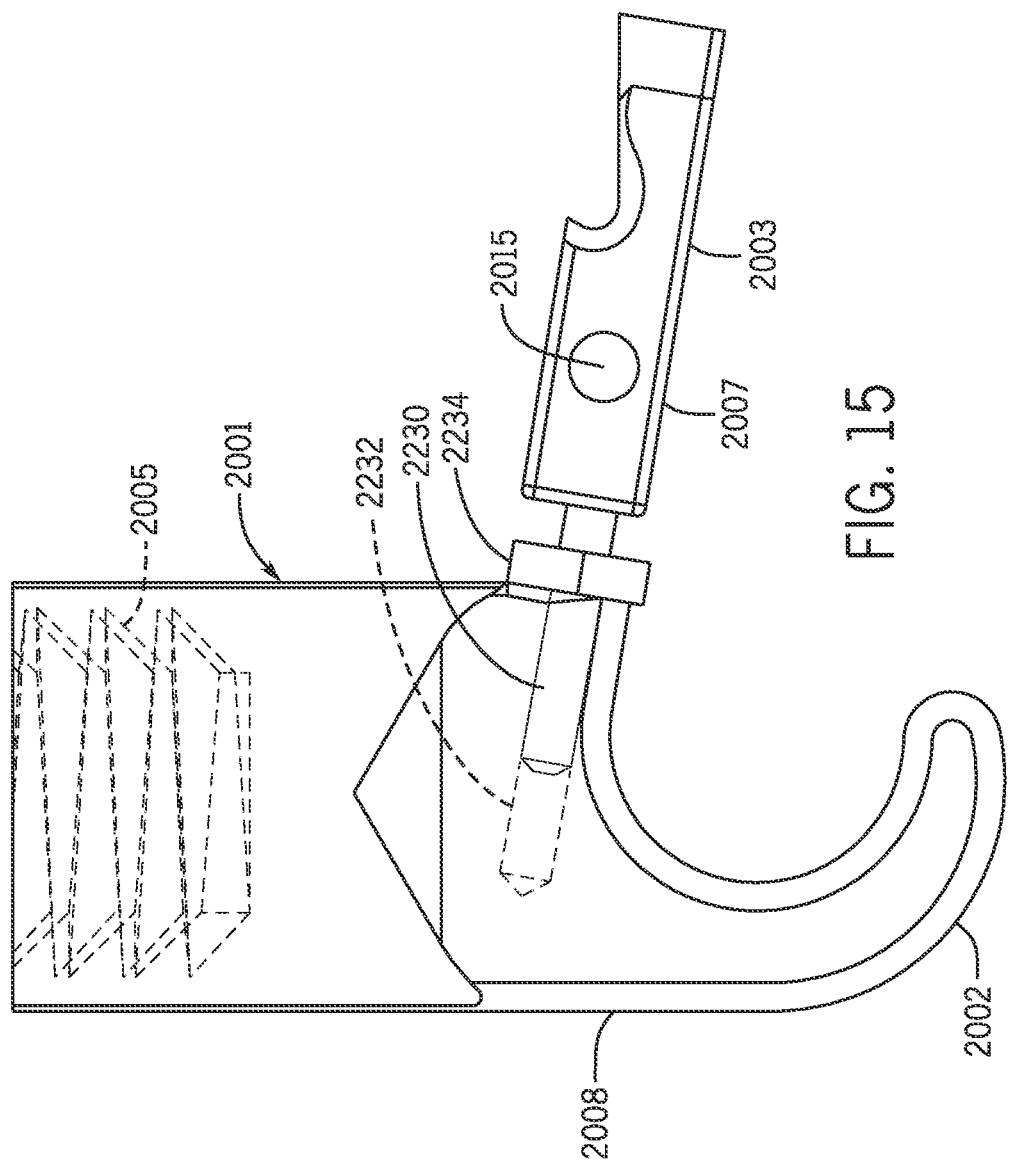

ADJUSTABLE SCREW-CLAMP ORTHOPEDIC APPARATUS

CROSS-REFERENCE TO RELATED PATENT APPLICATIONS

The present application is a U.S. National Stage of International Application No. PCT/US2015/026165 filed on Apr. 16, 2015, which claims the benefit of U.S. Provisional Patent Application No. 61/980,265 filed on Apr. 16, 2014, the entire disclosures of all of which are incorporated herein by reference.

FIELD

The present application relates generally to screw-clamp apparatus.

BACKGROUND

Due to the unique anatomy of the posterior thoracic spine, providing instrumentation for applying corrections to the spine, through for example fusion devices, presents numerous challenges. Some instrumentation for engaging in various spinal corrective procedures includes nonsegmental hook constructs, such as Harrington rods. The implementation of these rods has potential adverse results, such as flat-back deformity, hook pull out or dislodgement and high nonunion rates. Other hook constructs, such as Cotrel-Dubosset, allow for segmental fixation and better curve correction and control; however, these constructs cause a relatively high pseudoarthrosis rate to occur due to the large number of hooks displacing bone grafts, which are required with these constructs for biological fusion to take place. Such systems have also proven to be exceptionally difficult to remove or revise. Hybrid constructs may be implemented that use pedicle screw instrumentation in the distal thoracic spine and hook fixation or sublaminar wire fixation in the proximal and mid-thoracic spine, but are still complicated by the aforementioned issues related to the hook and screw implementation described.

Thoracic pedicle screw instrumentation implementation has increased due to the increase in construct rigidity and scoliosis correction. Pedicle screw constructs may have a risk of neurological or vascular injury if they are misplaced. Studies have found that the more proximal screws were at greater risk of malposition where the pedicles may have abnormal morphology. Other studies have found that on average over 12% of screws were misplaced of which half of those were of concern (adjacent or impinging the aorta or other viscera, or within the spinal canal adjacent or impinging the spinal cord). To overcome the risks of thoracic pedicle screw instrumentation, some authorities suggest the use of intraoperative CT scans. Successful image guidance navigation systems may need to visualize the entire thoracic spine during deformity surgery. This typically requires 4 or 5 intraoperative CT scans for a typical patient. The relatively high radiation exposure of multiple CT scans, when used in various patients such as the typical female adolescent, is a concern as this is the time when these patients are at greatest risk for radiation induced breast or other cancers given that they are still growing and unshielded.

In elderly patients or adults with osteoporosis, pedicle screw constructs have a potential risk of screw pullout and may need augmentation with bone cement. Some spine surgeons may opt to use sublaminar wires or hook instrumentation at the end vertebra to reinforce the pedicle screws. However, even well placed screws are a risk for osteoporosis patients due to the potential of "plowing" of the pedicle screws out of the pedicles and subsequently affecting the adjacent vascular structures.

Another potential problem in deformity patients treated with pedicle screw constructs is an increased risk for proximal junctional kyphosis, PJK. There is a loss of thoracic kyphosis associated with thoracic pedicle screw constructs. Chronic PJK may be secondary to this iatrogenic thoracic lordosis as the spine tries to balance itself in patients treated with screw constructs.

SUMMARY

According to one embodiment, a screw-clamp apparatus may include a first clamp component comprising a first attachment end and at least one hook on a first hook end, a second clamp component comprising a second attachment end and at least one hook on a second hook end, a bone-screw hole located in one of the first clamp component and the second clamp component, a bone screw configured to be inserted through the bone-screw hole and to be inserted into bone, a first spacer-receiver located on one of the first clamp component and the second clamp component, and a length-adjusting mechanism configured to adjust a longitudinal length of the screw-clamp apparatus. The first attachment end and the second attachment end are configured to attach the first clamp component and the second clamp component together. The first spacer-receiver is configured to secure a spacer.

According to another embodiment, a screw-clamp apparatus includes a first clamp component comprising a first attachment end and at least one hook on a first hook end, a second clamp component comprising a second attachment end and at least one hook on a second hook end, a bone-screw hole located in one of the first clamp component and the second clamp component, a bone screw configured to be inserted through the bone-screw hole and to be inserted into bone, a first spacer-receiver located on the first clamp component, and a second spacer-receiver on the second clamp component. The first attachment end and the second attachment end are configured to attach the first clamp component and the second clamp component together. The first spacer-receiver and the second spacer-receiver are configured to secure a spacer.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

These and other features, aspects, and advantages of the present invention will become apparent from the following description, appended claims, and the accompanying exemplary embodiments shown in the drawings, which are briefly described below.

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 1A and 1B are side and front views of a human spine.

FIG. 5 is a perspective view of screw-clamp apparatus interconnected by a spacer and engaged with a human spine according to one embodiment.

FIG. 6A is a perspective view of the screw-clamp apparatus of FIG. 5.

FIGS. 7A-7B illustrate perspective, exploded views of the clamp component of the screw-clamp apparatus of FIG. 5 including a bushing, c-clip and a bone-screw hole for fitting a bone screw therein.

FIGS. 8A-8C illustrate partial cut away, side views of the screw-clamp apparatus of FIG. 5 in various positions related to transitioning from an open state to a closed state as a screw is tightened within the screw-clamp apparatus, in accordance with an exemplary embodiment.

FIG. 9 provides an exploded, perspective view of the screw-clamp apparatus of FIG. 5 with a spacer, in accordance with an exemplary embodiment.

FIG. 15 illustrates a side view of a clamp component according to one embodiment.

Figure 2:
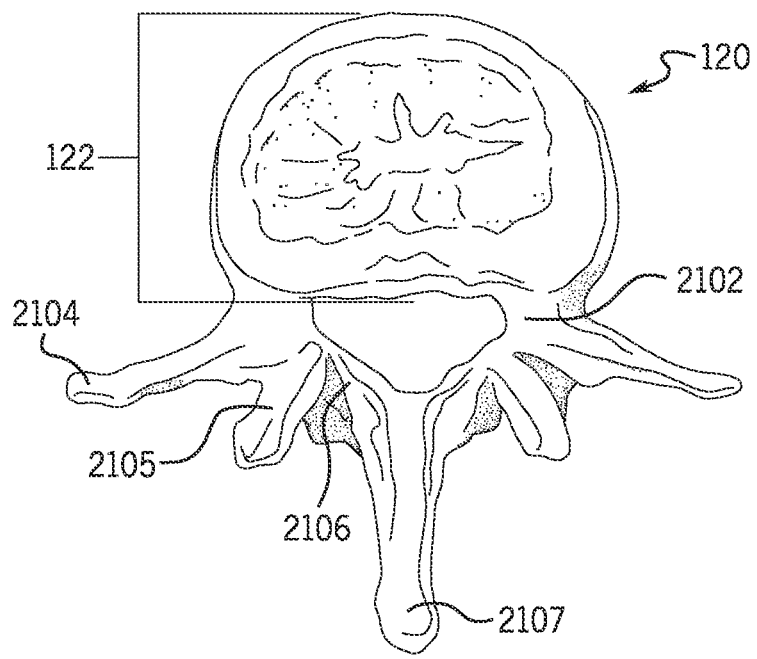
FIG. 2 is a top view of a human vertebrae from the spine of FIG. 1A.

The features and advantages of the inventive concepts disclosed herein will become more apparent from the detailed description set forth below when taken in conjunction with the drawings.

DETAILED DESCRIPTION

Following below are more detailed descriptions of various concepts related to, and embodiments of, inventive apparatuses and methods for a screw-clamp apparatus. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Referring generally to the Figures, various embodiments of a screw-clamp apparatus are shown. Inventive embodiments illustrated and described herein act as a "claw" to the lateral mass of the thoracic vertebra. Various embodiments of the screw-clamp apparatus or device allow the ease of use that may be associated with hooks but give rigidity akin to that of a pedicle screw without the same level of risks of injury to the spinal cord, aorta, adjacent viscera or risk of pullout in osteoporotic patients. The present invention may be used to realign or straighten the spine. For example, the screw-clamp apparatus may be used to treat and correct orthopedic and/or spinal defects, like scoliosis, which is the side-to-side or lateral curvature of the spine.

Human Anatomy

As shown in FIGS. 1A and 1B, the spine 2101 of the human body is categorized into five regions of vertebrae 120. The cervical vertebrae 112 (including vertebrae C1-C7) generally comprises the neck region of the spine and is connected to the base of the skull. The thoracic vertebrae 114 (including vertebrae T1-T12) generally comprises the upper back region of the spine. The lumbar vertebrae 116 (including vertebrae L1-L5) generally comprises the lower back region of the spine. The sacrum 118 and coccyx 119 generally comprise the lowermost portion of the spine and the tailbone and include fused vertebrae.

Figure 3:
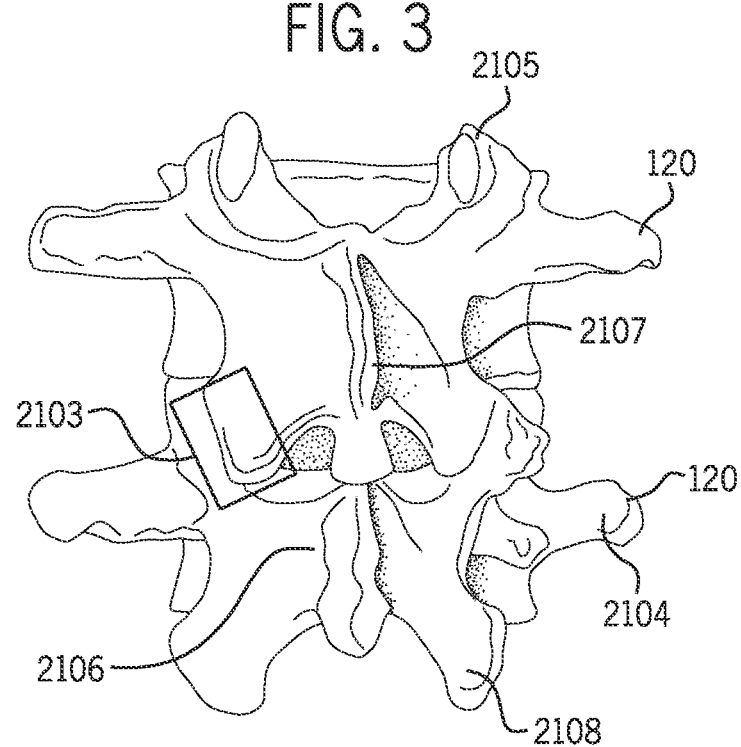
FIG. 3 is a back view of two human vertebrae from the spine of FIG. 1A.

As shown in FIGS. 2 and 3, a vertebrae 120 of the spine 2101 may include multiple different regions or bones. The body 122 of the vertebrae 120 may at least partially support the various components of the vertebrae 120. For example, the vertebrae 120 may include a facet joint 2103, a transverse process 2104, a superior articular process 2105, a lamina 2106, a spinous process 2107, inferior articular process 2108, a lateral mass, and a pedicle 2102.

Attaching the Screw-Clamp Apparatus to the Spine

Figure 4:
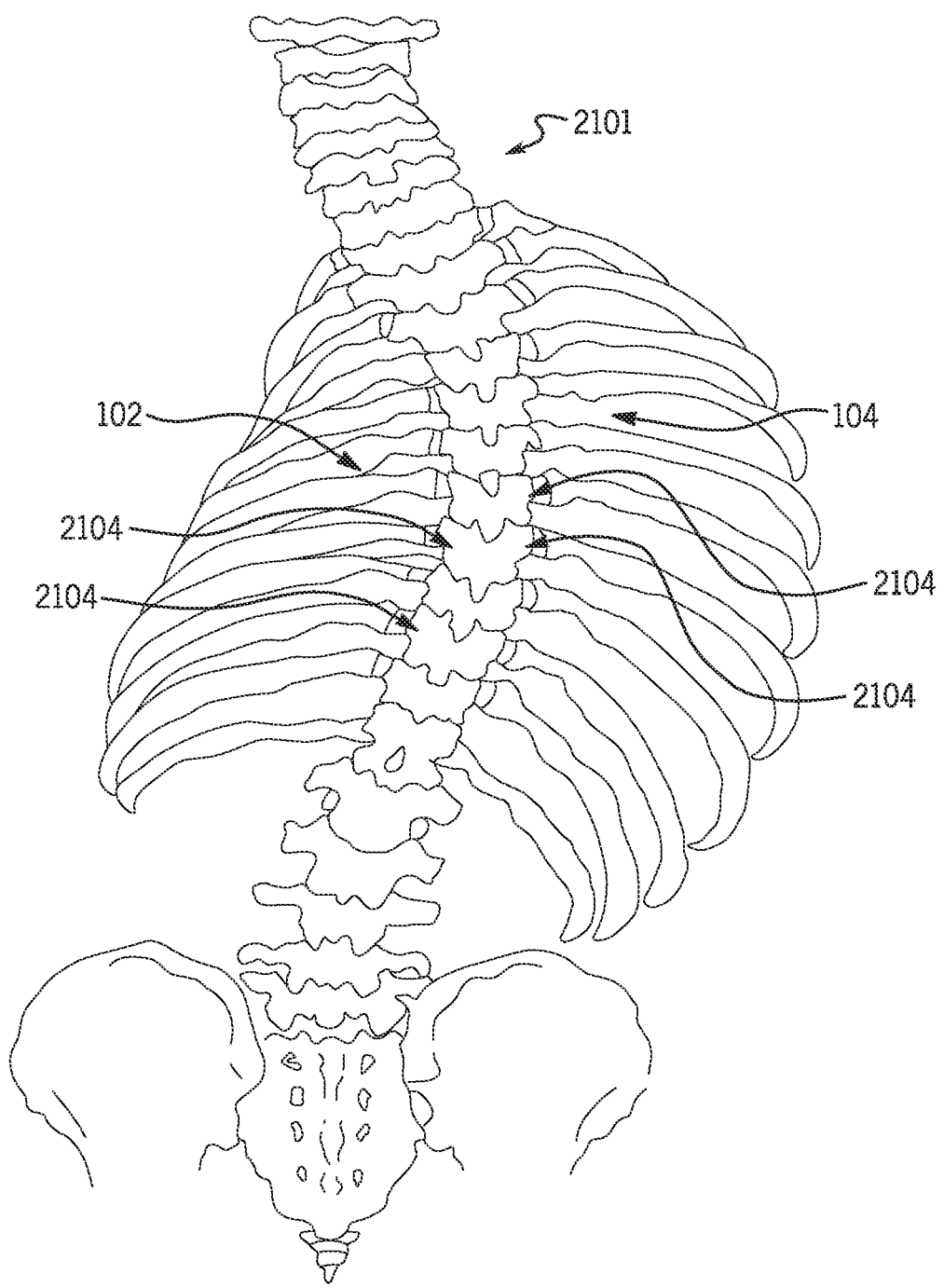
FIG. 4 is a back view of a human scoliotic spine.

A spine 2101 with an abnormal curvature along the length of the spine 2101 (due to, for example, scoliosis) is shown in FIG. 4. For example, the spine 2101 shown in FIG. 4 has a concave aspect 102 and a convex aspect 104.

Screw-clamp apparatus or devices may be used to correct the abnormal curvature of a spine 2101 by clamping multiple screw-clamp apparatus to at least a portion of the spine 2101 and interconnecting them with a connecting rod or spacer to realign or correct the spine 2101 along its length. Multiple screw-clamp apparatus may be used to further support the spine 2101, in particular in the case of premature degeneration or deterioration. Simplified versions of a screw-clamp apparatus 2000 and spacer 2051 are shown in FIG. 5 to explain the attachment of the apparatus to the spine.

The screw-clamp apparatus 2000 may be positioned and connected along a lengthwise or longitudinal direction of the spine 2101 such that the spacer 2051 may span at least a portion of the length of the spine 2101. As described in more detail below, the screw-clamp apparatus 2000 may clamp around a portion of bone of the spine 2101, such as parts of the vertebrae 120, and may further be screwed into the spine 2101.

The screw-clamp apparatus 2000 can be connected over multiple segments of the thoracic spine or vertebrae 114. However, it is anticipated that the screw-clamp apparatus 2000 may attach to vertebrae 120 along any region of the spine 2101. For example, the screw-clamp apparatus 2000 is configured to fit to the spine as shown in FIG. 5 with the clamp arm/spacer-receiver portion (the first clamp component 2001) hooking into the spinal facet joints 2103 and the proximal "claw" (the second clamp component 2010) closing around the laminas (not shown) with the medial downward hook 2012 (hook 2012 is shown in subsequent figures) and around the transverse process 2104 with the lateral oblique downward hooks 2011. Alternatively or additionally, at least one of the clamp components 2001 and 2010 may attach to a lateral mass of the vertebrae. In FIG. 5, the proximal clamp component 2010 (toward the head) is left and is asymmetrical, as shown according to the illustrated embodiments. However, it is anticipated that hooks 2002 and hooks 2011 and 2012 may be configured to attach to other portions or segments of the vertebrae 120.

Small bone screws 2020 (which include bone-screw heads 2021) may be directed towards or screwed into pedicles 2102 (which may be disposed below the screw-clamp apparatus 2000 in FIG. 5, depending on the screw-clamp apparatus' positioning and orientation). Screwing the bone screw 2020 into the pedicles 2102 may simply connect the screw-clamp apparatus to the spine 2101 or may cause the claw constructs of the screw-clamp apparatus 2000 to close snugly around the bilateral masses or bone (as explained in more detail below).

Clamp Components of the Screw-Clamp Apparatus

A simplified embodiment of a screw-clamp apparatus 2000 is shown in FIG. 6A. The screw-clamp apparatus 2000 has a first or distal clamp component 2001 and a second or proximal clamp component 2010 that are configured to attach around bone of the spine 2101.

Hooks of the Clamp Components

The first clamp component 2001 may include a first bone hook end 2008 with at least one hook 2002 configured to attach to or hook at least partially around bone. The second clamp component 2010 may include a second bone hook end 2018 with at least one hook 2011 and/or 2012 configured to attach to or hook at least partially around bone. An example of the attachment of the hooks 2002, 2012 to the spine 2101 is shown in FIG. 5.

The first or distal clamp component 2001 may have at least one up-going or upwardly angled hook 2002 extending, at least in part, in a vertical direction (the z-axis) from the first hook end 2008, as shown in FIG. 6A. Preferably, the first clamp component 2001 has two such hooks 2002, as shown in FIG. 7A Hooks 2002 may fit into, attach to, or hook at least partially around a bone. For example, hooks 2002 may hook around a portion of the spine, such as a facet joint 2103 on the vertebrae 120. Hooks 2002 may also attach to a bone graft.

The at least one hook 2002 may extend from any portion of the clamp component 2001. The hook 2002, which may be positioned or manufactured to be located anywhere along the clamp component 2001, such as along the longitudinal midline of the clamp component 2001. The at least one hook 2002 may extend from the clamp component 2001 along the vertical direction or z-axis and may further extend at least partially along the longitudinal direction or x-axis. The hook 2002 may further extend at least partially back into the z-axis along the length of the hook 2002, such that the hook 2002 generally makes a "C" shape. Optionally, the hook 2002 may extend at least partially along the lateral direction or y-axis. The hook 2002 may be curved or may include straight segments.

Figure 7B:
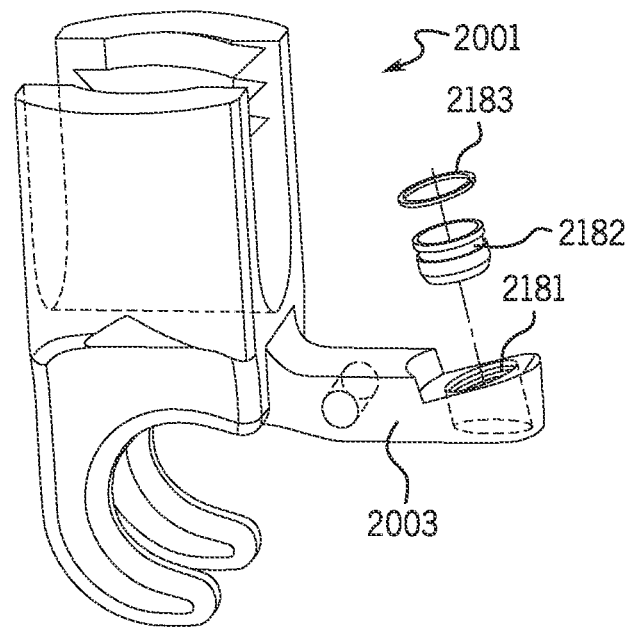
Figure 7C:
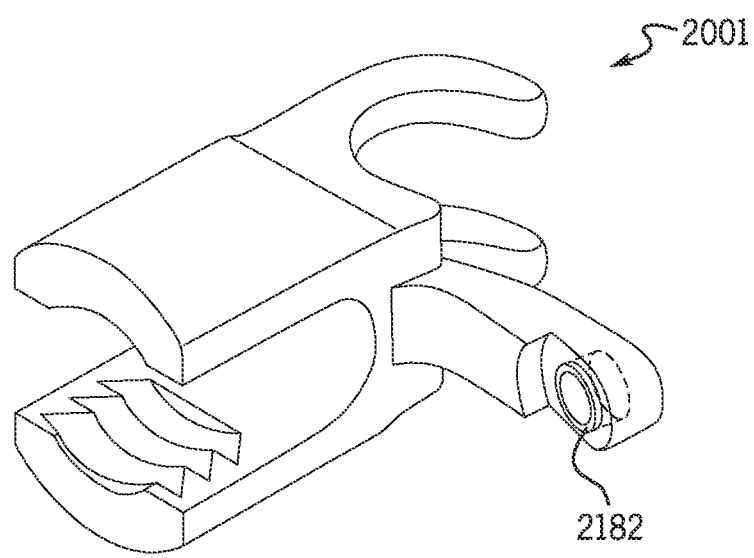
FIGS. 7C-7D illustrate a perspective angled view and a front view, respectively, of the clamp component of FIG. 7A.
Figure 7D:
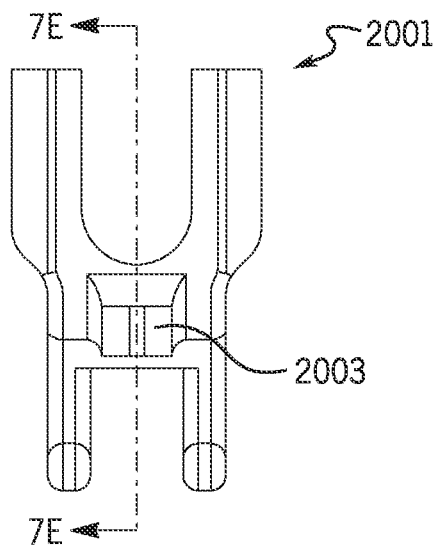
Figure 7E:
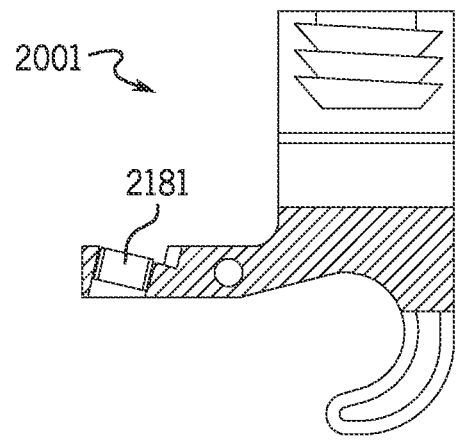
FIG. 7E is a cross-sectional view through Section 7E and FIG. 7F is a side view of the clamp component of FIG. 7D.
Figure 7F:
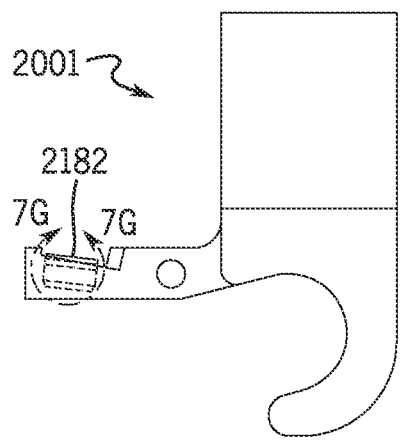
Figure 7G:
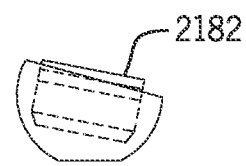
FIG. 7G is an enlarged view of Section 7G of FIG. 7F of a bone-screw hole and bushing of the clamp component.
Figure 7H:
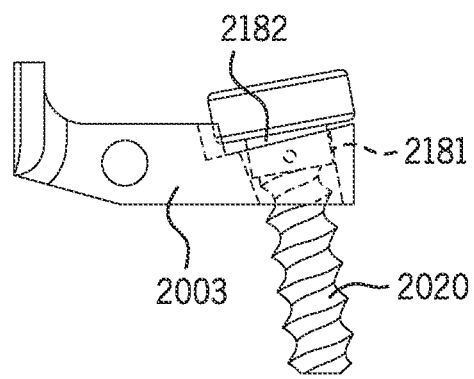
FIG. 7H is a side view of an arm of the clamp component of FIG. 7A with a screw, including a bone-screw hole and a bushing for fitting therein, in accordance with an exemplary embodiment.

In the illustrated embodiment in FIG. 7D, clamp component 2001 is a symmetrical component with respect to a midline extending between hooks 2002 as will be demonstrated further herein. The hooks 2002 may further be parallel to each other. However, it is anticipated that the hooks 2002 may be asymmetrical about a longitudinal midline of the clamp component 2001.

The second or proximal hinged clamp component 2010 also has at least one hook 2011, 2012, and preferably dual hooks (similar to the hooks 2002 of the first clamp component 2001), extending, at least in part, in a vertical direction (the z-axis) from the second hook end 2018, as shown in FIG. 6A. The hooks include a medial down-going hook 2012 configured to engage the lamina and a lateral down-going hook 2011, extending, at least in part, in a vertical direction (the z-axis) from the second hook end 2018. The hooks 2011, 2012 may be sized or oriented according to the desired configuration. For example, it may be desirable for the hooks 2011, 2012 to attach to other bones or portions of the vertebrae 120. In the illustrated embodiment, clamp component 2010 is an asymmetrical clamp component with respect to a midline extending between hooks 2011 and 2012 (along the longitudinal axis).

Figure 6B:
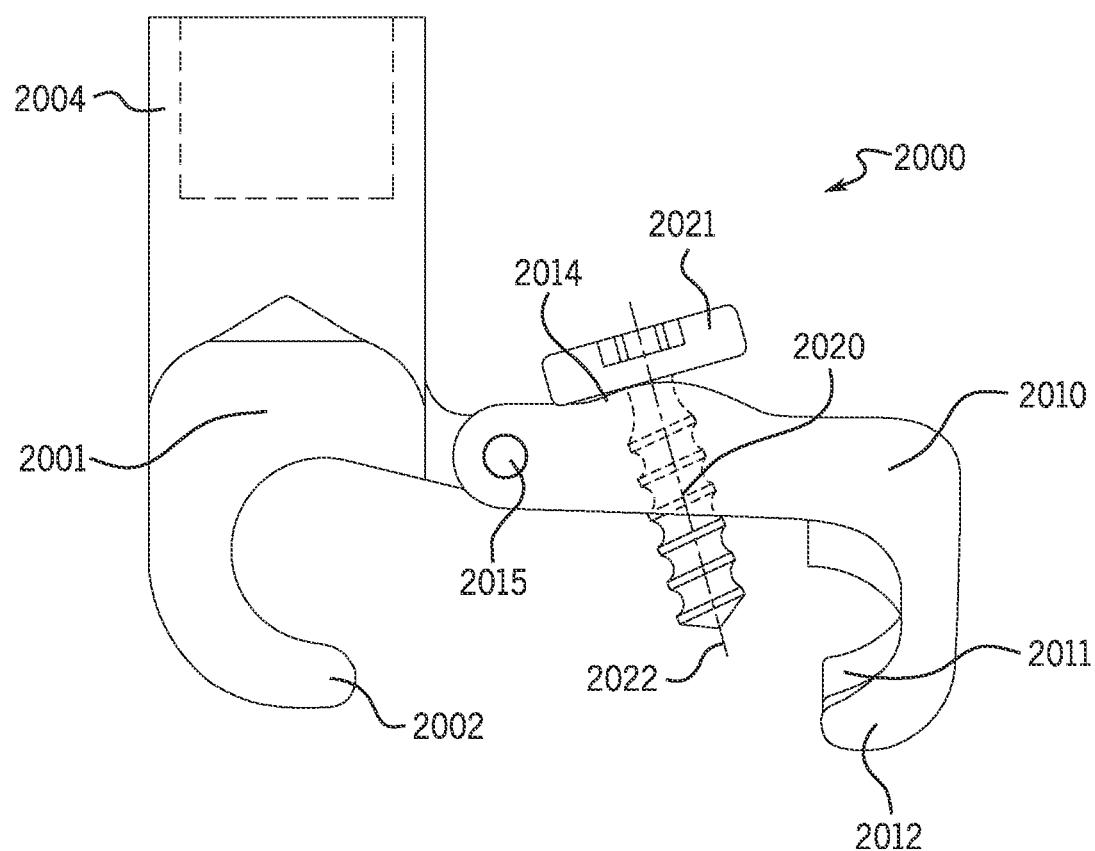
FIGS. 6B-6D are side, rear (back), and top wire-frame depictions, respectively of the screw-clamp apparatus of FIG. 5.
Figure 6C:
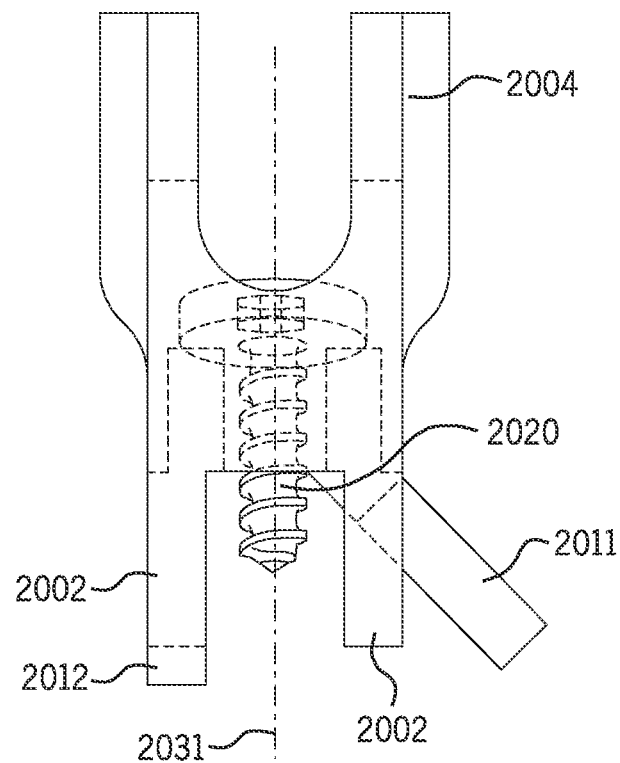
Figure 6D:
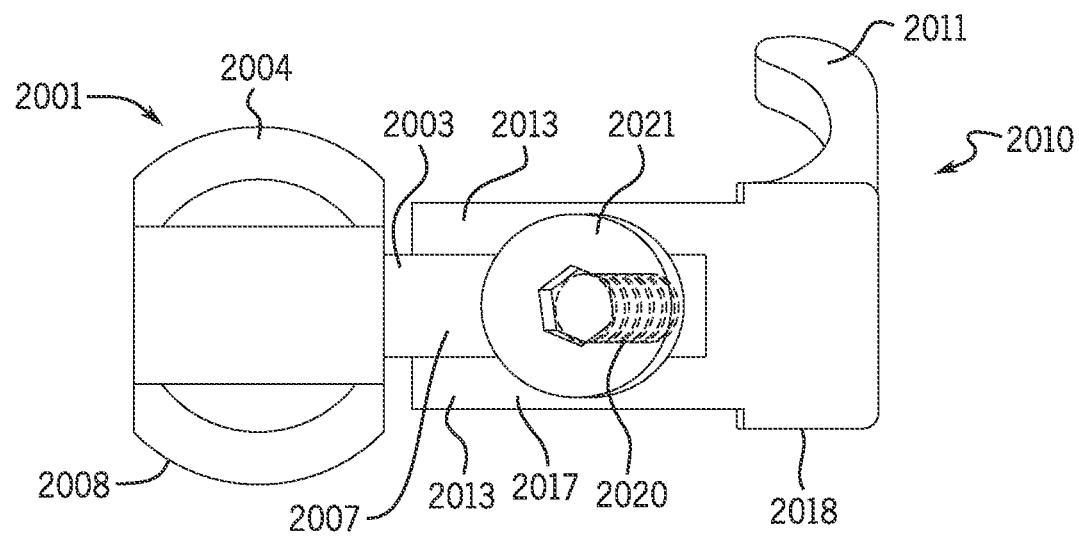

As depicted in FIG. 6C, lateral hook 2011 extends in a lateral direction from clamp component 2010, while hooks 2002 and hook 2012 extend downwardly from the clamp components in the vertical direction. The lateral extension of lateral hook 2011 is also illustrated in FIG. 6D. Accordingly, clamp component 2010 is asymmetrical with respect to a midline 2031.

Hooks 2002 and hooks 2011, 2012 may be positioned or oriented such that the hooks open up toward each other to allow the screw-clamp apparatus 2000 to clamp at least partially around bone between the hooks. It is anticipated that the clamp component 2001 and the hooks 2011 and 2012 may be configured or shaped according to the desired configuration, similar to that of the clamp component 2010 and hooks 2002.

It is also anticipated that the clamp components 2001 and 2010 may be manufactured as a single, integral piece with the hooks 2002 and 2011, 2012, respectively, or may be a separate piece from the hooks 2002 and 2011, 2012, respectively, and later connected together.

Connecting the Clamp Components

The first clamp component 2001 and the second clamp component 2010 may be connected or attached such that they are pivotable, hingable, or slidable relative to each other.

For example, first clamp component 2001 and the second clamp component 2010 may include a pin and aperture arrangement that provides a pivotal connection.

In a preferred embodiment shown in FIGS. 6D and 8A-8C, the first clamp component 2001 includes a first clamp component attachment end 2007 with at least one arm 2003, and the second clamp component 2010 includes a second clamp component attachment end 2017 with at least one clamp arm 2013. FIG. 6D shows how the arm 2003 of the clamp component 2001 may be positioned between the clamp arms 2013 of the clamp component 2010. As shown in FIGS. 6A and 9, a pin 2015 projecting from the arm 2003 can be positioned to extend through corresponding apertures or holes in the arms 2013 of the clamp component 2010 along the y-axis, such that the clamp components 2001 and 2010 may rotate with respect to each other along the x-axis and z-axis.

Such a pin and aperture arrangement can be utilized in other embodiments. For example, in the embodiment shown in FIG. 15, a pin 2015 projecting from an arm 2003 of a first clamp component 2001 can project into apertures of at least one clamp arm 2013 of a second clamp component 2010 (not shown). Similarly, in the embodiment shown in FIGS. 16A-16D, a pin 2015 projecting from an arm 2003 of a first clamp component 2001 can project into apertures of at least one clamp arm 2013 of a second clamp component 2010.

Figure 14A:
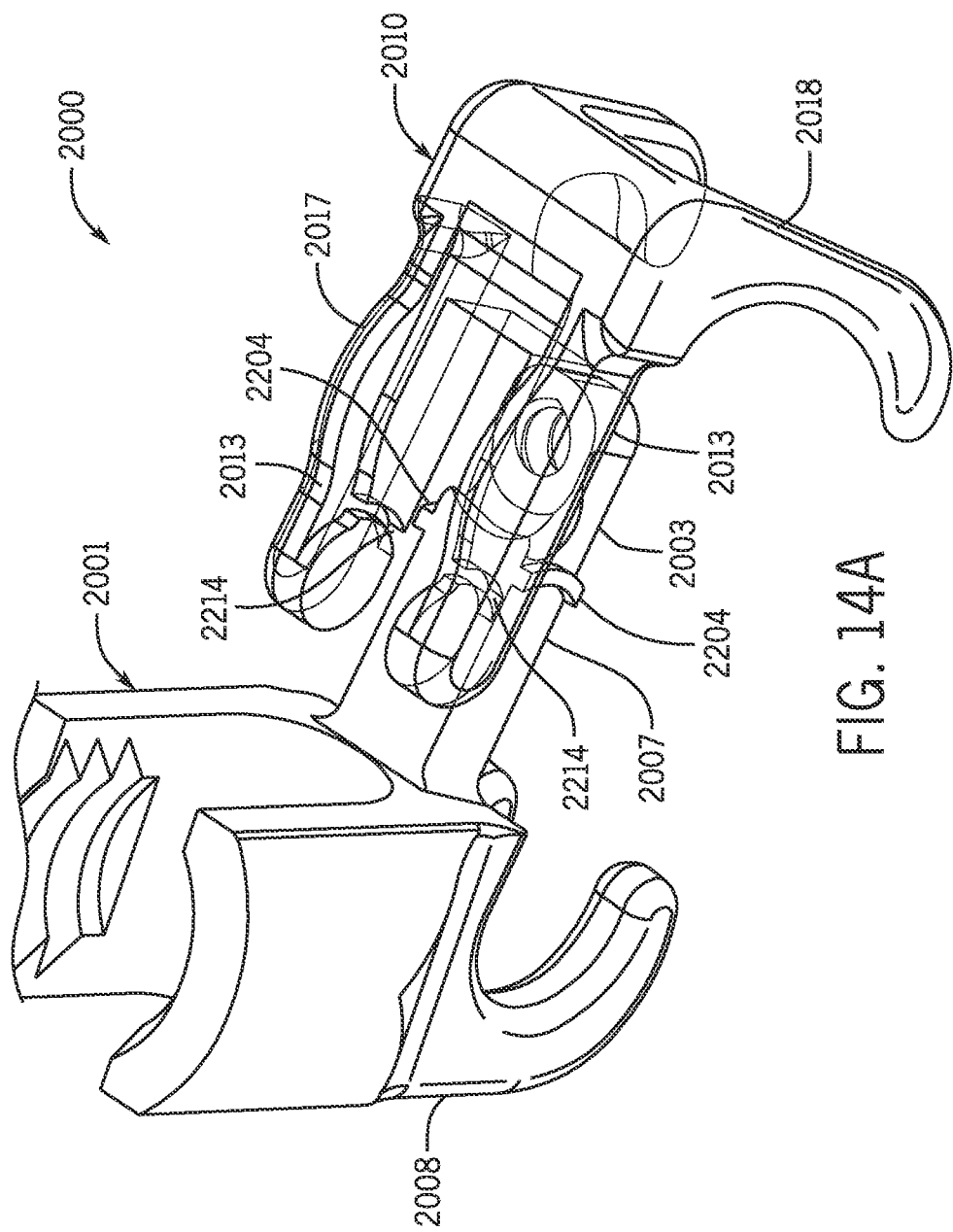
FIGS. 14A and 14B illustrate perspective and side views of a screw-clamp apparatus with a recessed cam surface according to one embodiment.
Figure 14B:
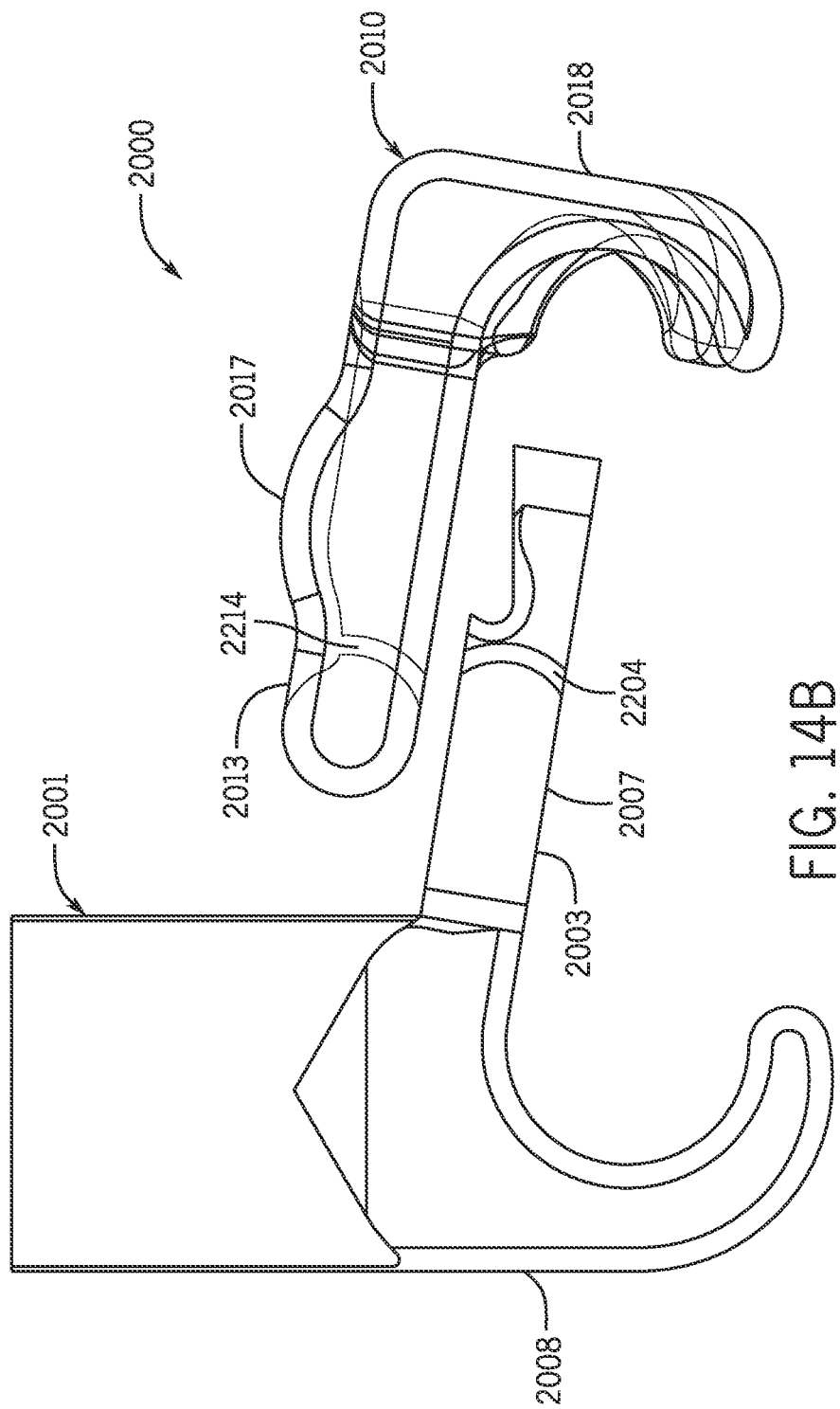

In another preferred embodiment shown in FIGS. 14A and 14B, the first clamp component 2001 and the second clamp component 2010 may include a pin and groove arrangement that provides a pivotal connection, the screw-clamp apparatus 2000 may include pins or a prominent portion 2204 on the first attachment end 2007 that is movable at least partially within a channel or groove 2214 on the second attachment end 2017 to allow the first and second clamp components 2001 and 2010 to pivot relative to each other. More specifically, as shown in FIG. 14A, the arm 2003 may include at least one prominent portion 2204, which may slide at least partially within the groove 2214 located on the arm 2013 as the clamp component 2010 is pivoted or rotated relative to the clamp component 2001. Alternatively, the prominent portion 2204 may be located on the arm 2013 and the groove 2214 may be located on the arm 2003. The prominent portion 2204 and the groove 2214 may be shaped according to the desired configuration. As shown in FIG. 14A, the prominent portion 2204 and the groove 2214 are "C" shaped and complementary to each other to allow the clamp components 2001 and 2010 to pivot relative to each other. The degree of curvature of the arc of the prominent portion 2204 and the groove 2214 may be tailored during manufacturing according to the desired configuration. The prominent portion 2204 and the groove 2214 may further reduce the number of required components within the screw-clamp apparatus 2000, thereby reducing the risk of device failure or losing components of the screw-clamp apparatus 2000 within a body.

The various pivoting mechanisms may be positioned or manufactured to be located anywhere along the length of the arms 2003 and 2013, such that the length of the arms 2003 and 2013 (and thereby, the overall length of the screw-clamp apparatus 2000) may be tailored according to the desired configuration.

The clamp component 2001 may be integrally formed (e.g., manufactured as a single component) with arms 2003 and the clamp component 2010 may be integrally formed with its arm(s) 2013. However, it is anticipated that the clamp components 2001 and 2010 may be separate from and attachable or connectable with the arms 2003 and 2013, respectively, during or after the manufacturing process, such that the clamp components 2001 and 2010 may be separate components from the arms 2003 and 2013, respectively. Further, a variety of different sizes of clamp components 2001 and 2010 may be assembled together to create a screw-clamp apparatus 2000 with the desired overall size (e.g., length).

Figure 19A:
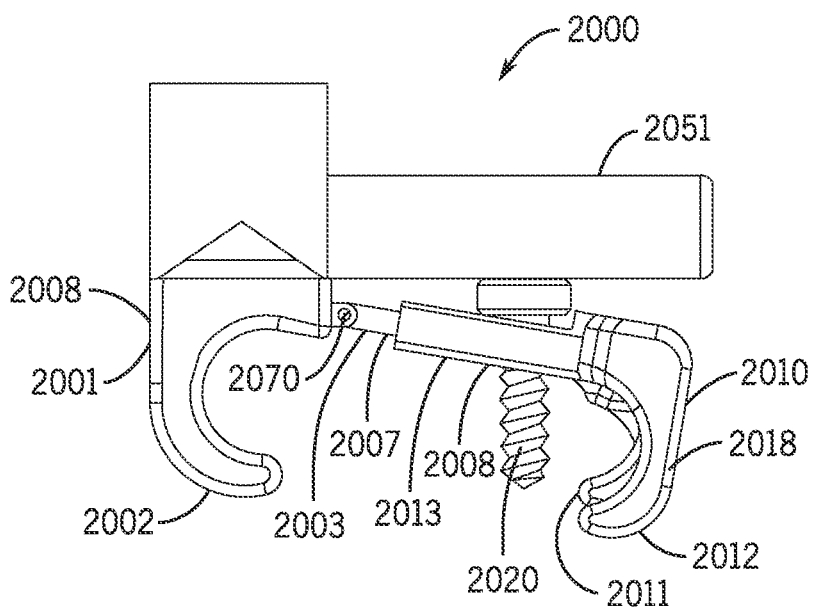
FIGS. 19A-19F illustrate a side view, a perspective view, a top view, a cross-sectional view (through Section 19D of FIG. 19C), a front view, and a cross-sectional view (through Section 19F of FIG. 19E), respectively, of a screw-clamp apparatus according to one embodiment.
Figure 19B:
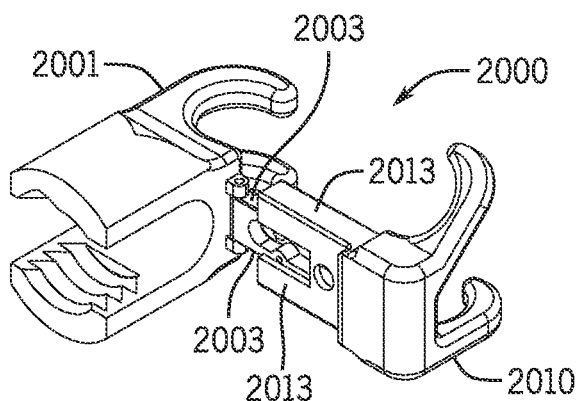
Figure 19C:
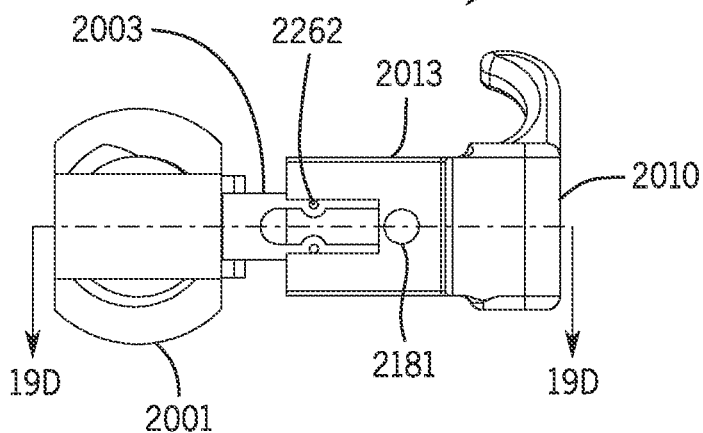
Figure 19D:
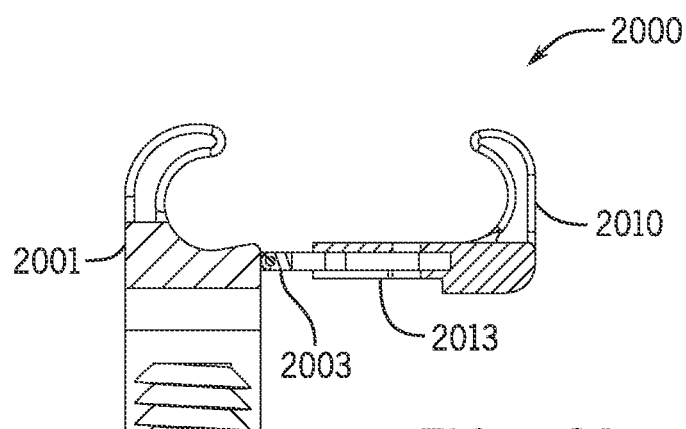
Figure 19E:
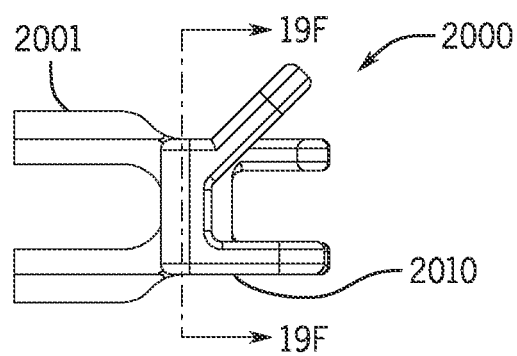
Figure 19F:
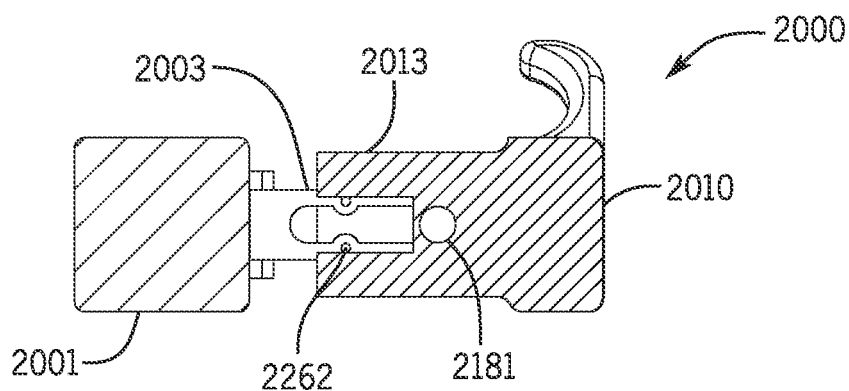
Figure 20A:
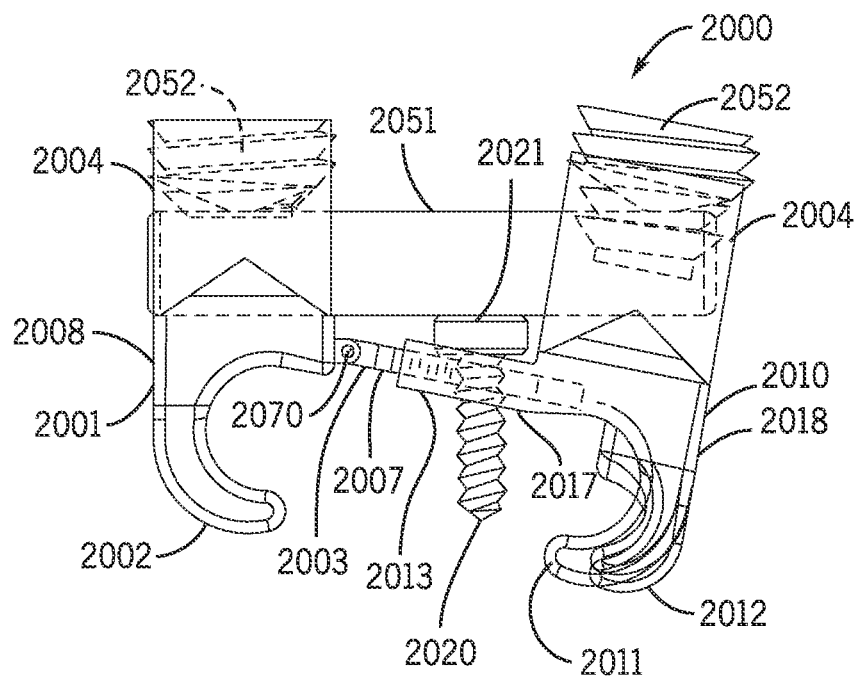
FIGS. 20A-20F illustrate a side view, a perspective view, a top view, a cross-sectional view (through Section 20D of FIG. 20C), a front view, and a cross-sectional view (through Section 20F of FIG. 20E), respectively, of a screw-clamp apparatus according to one embodiment.
Figure 20B:
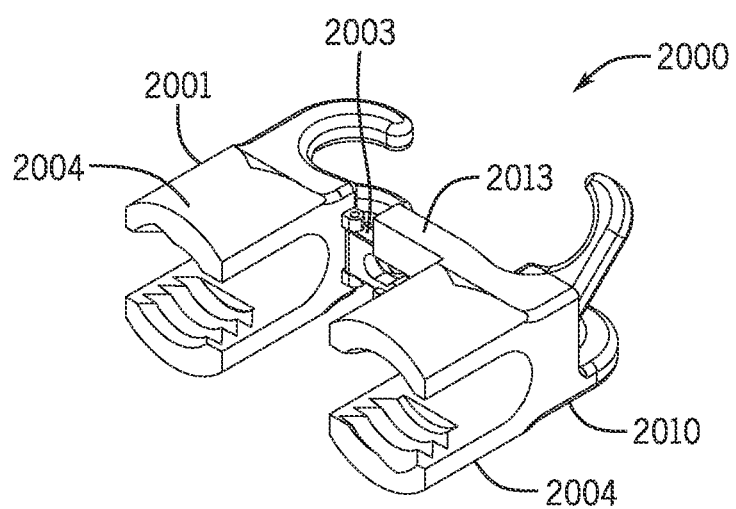
Figure 20C:
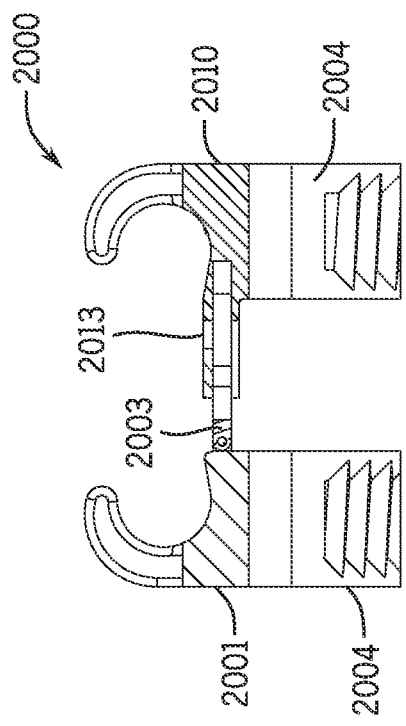
Figure 20D:
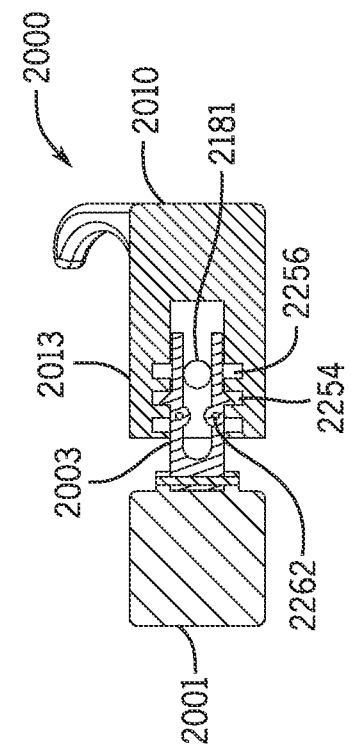
Figure 20E:
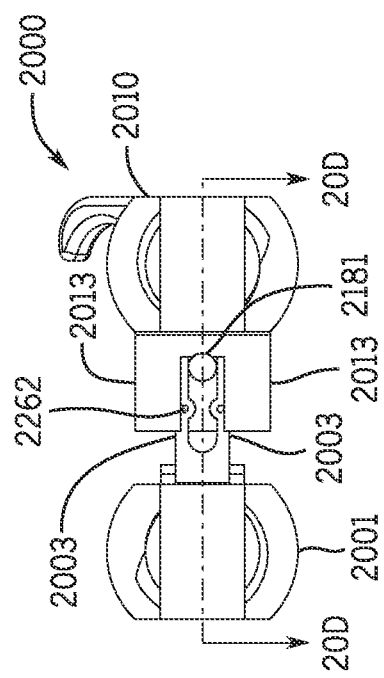
Figure 20F:
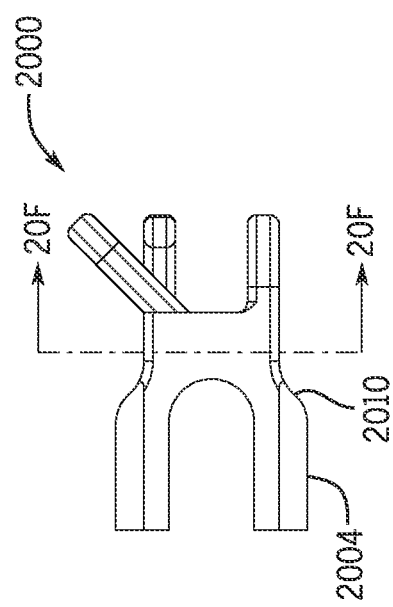
Figure 21A:
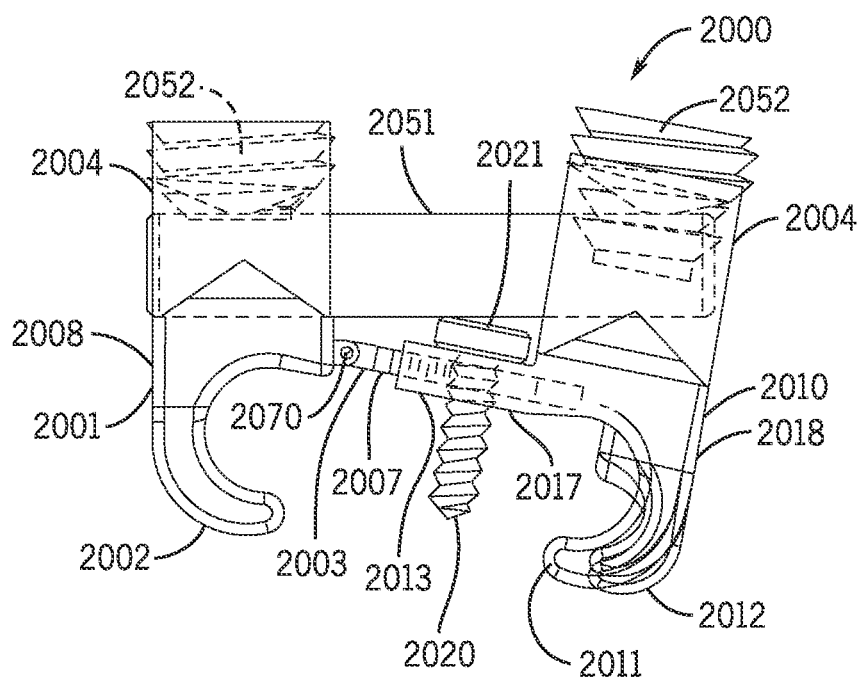
FIGS. 21A-21F illustrate a side view, a perspective view, a top view, a cross-sectional view (through Section 21D of FIG. 21C), a front view, and a cross-sectional view (through Section 21F of FIG. 21E), respectively, of a screw-clamp apparatus according to one embodiment.
Figure 21B:
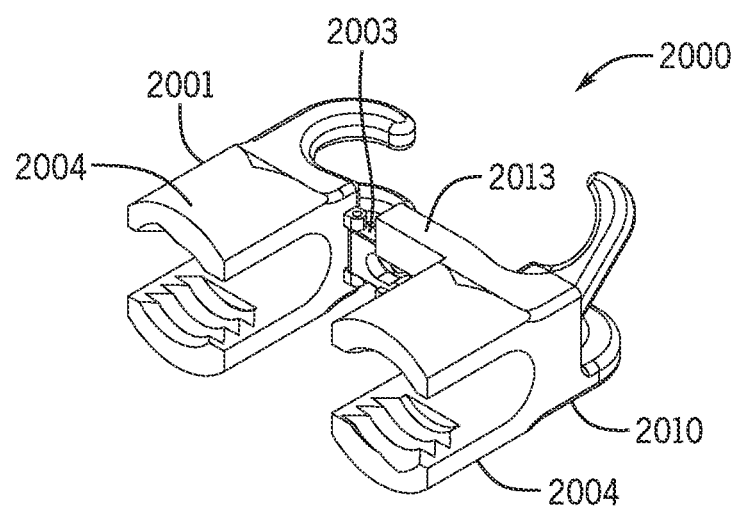
Figure 21D:
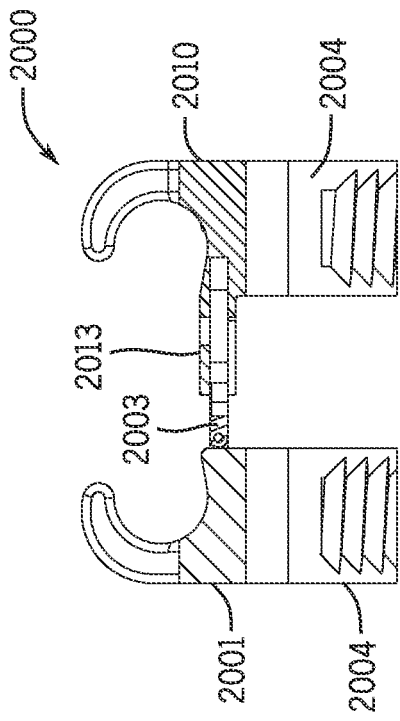
Figure 21F:
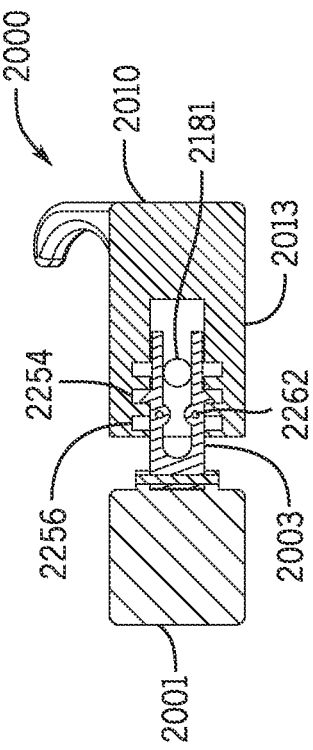
Figure 21C:
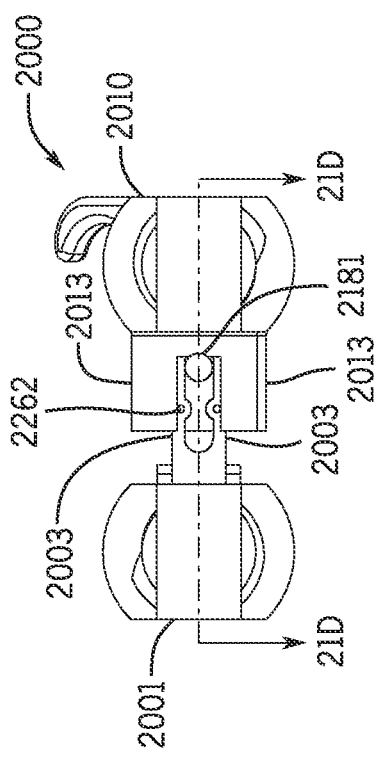
Figure 21E:
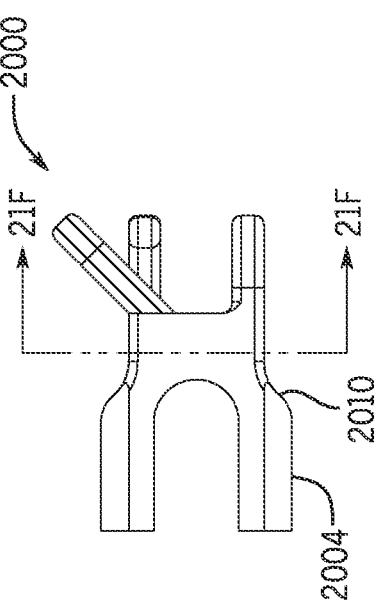
Figure 22A:
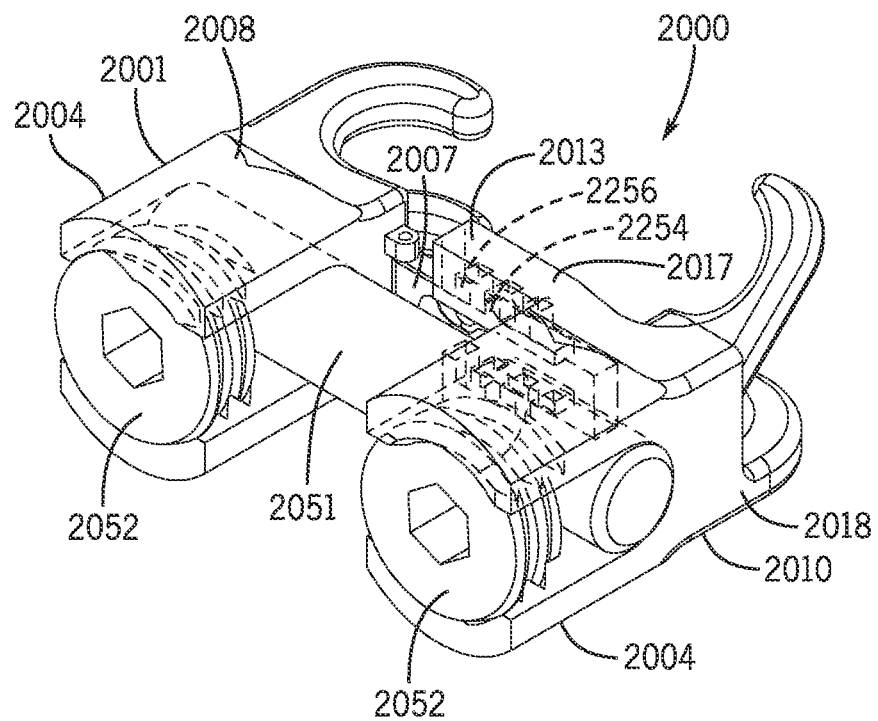
FIGS. 22A-22D illustrate a perspective view, a front view, a top view, and a partially cross-sectional view (through Section 22D of FIG. 22C), respectively, of a screw-clamp apparatus according to one embodiment.
Figure 22B:
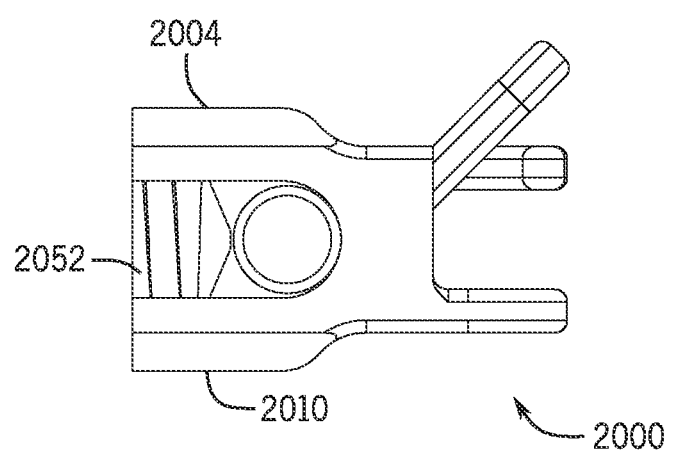
Figure 22C:
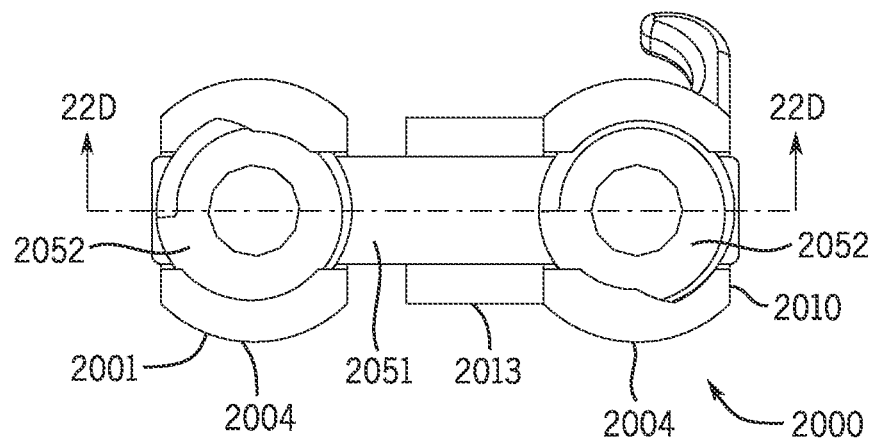
Figure 22D:
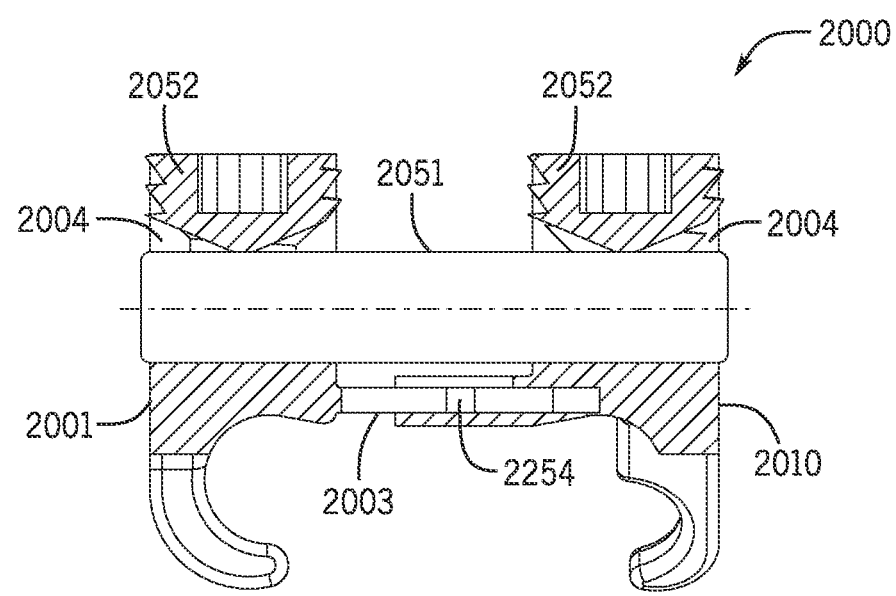
Figure 23A:
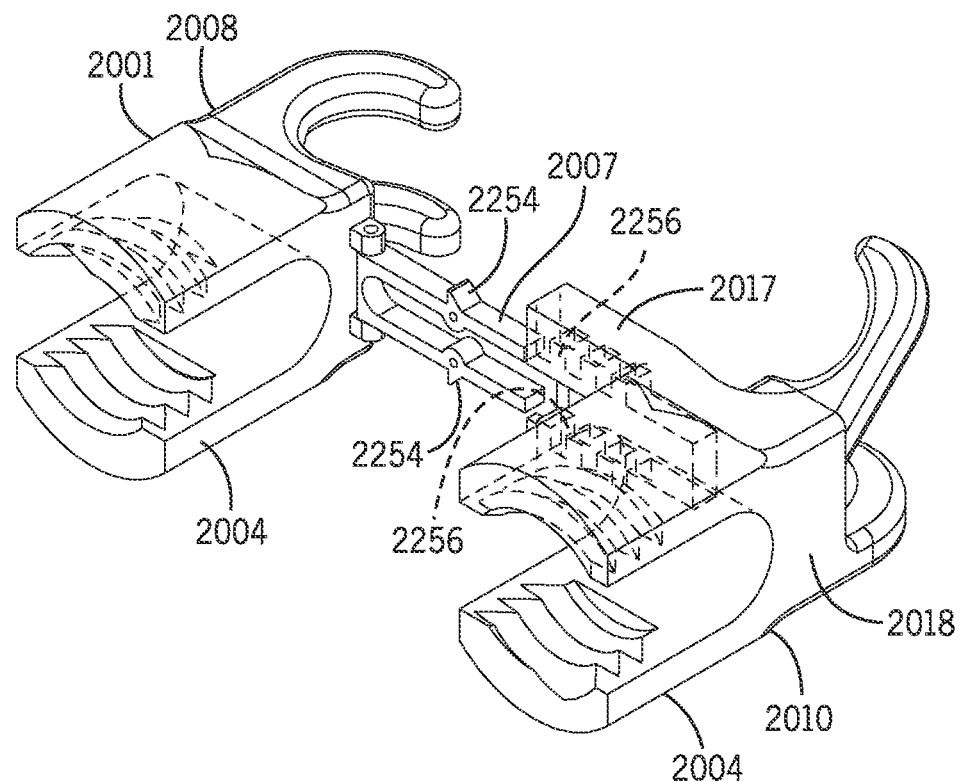
FIGS. 23A-23E illustrate a perspective view, a top view, a cross-sectional view (through Section 23C of FIG. 23B), a front view, and a cross-sectional view (through Section 23E of FIG. 23D), respectively, of clamp components that may be disposed within the screw-clamp apparatus of FIG. 22A.
Figure 23B:
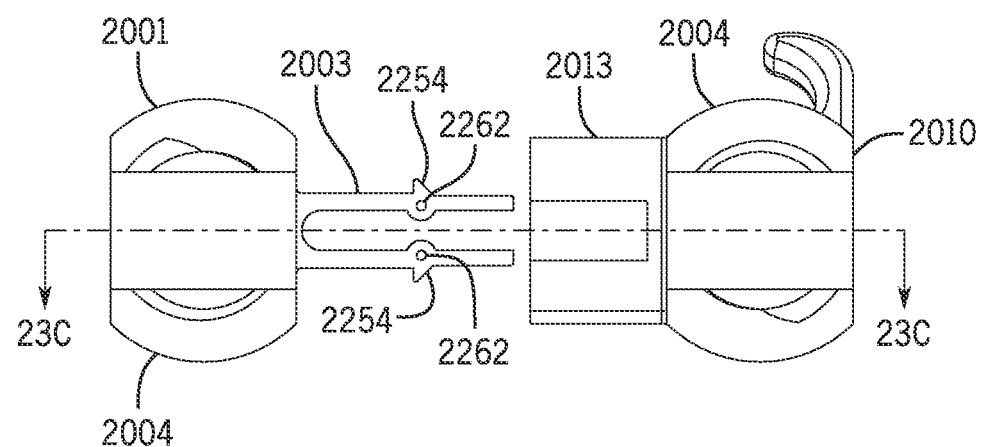
Figure 23C:
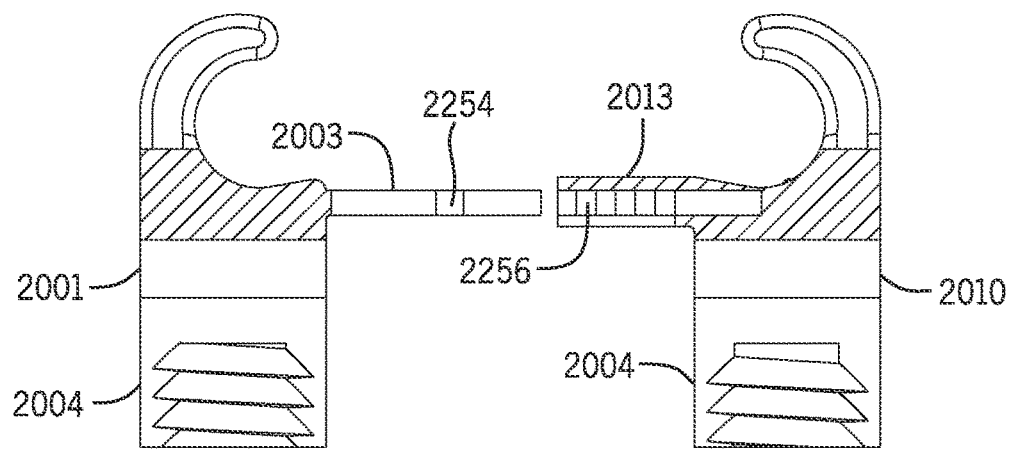
Figure 23D:
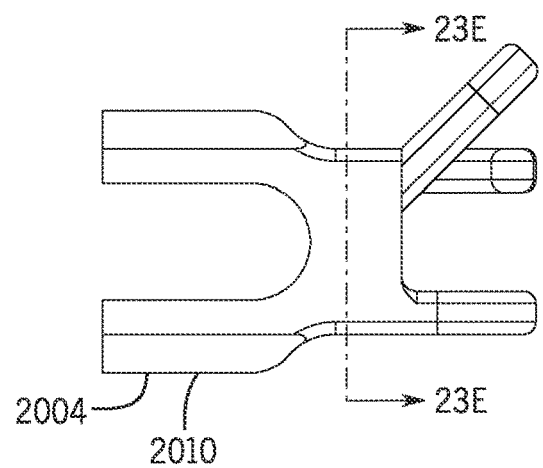
Figure 23E:
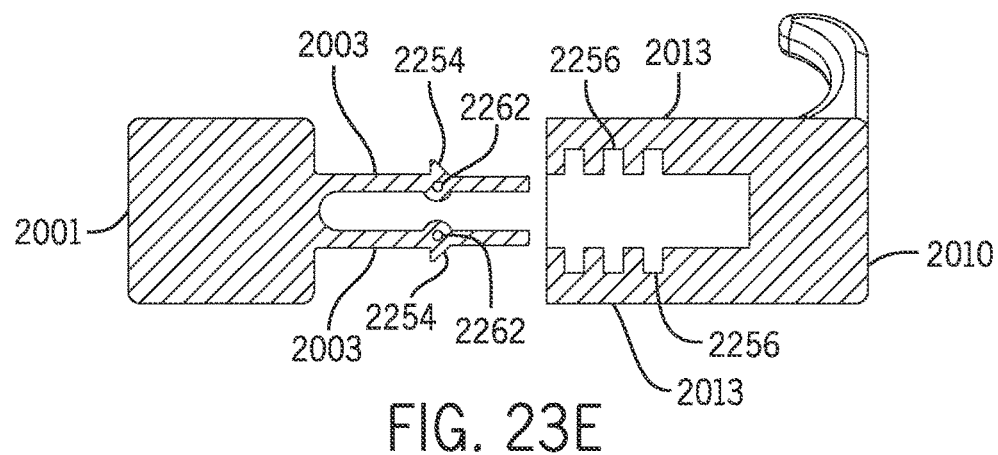

Alternatively or additionally, as shown in FIGS. 19A, 20A, and 21A, the first attachment end 2007 may be pivotally mounted to the first hook end 2008 through, for example, a hinge 2070 created by a pin and aperture arrangement, thereby allowing the arm 2003 to pivot with respect to the clamp component 2001. The arm 2003 can include apertures that receive a pin projecting from the first hook end 2008, or vice versa. The arm 2003 (as well as the clamp component 2010) may rotate approximately 10° with respect to the longitudinal or horizontal axis of the clamp component 2001. It is also anticipated that the arm 2013 may pivot with respect to the clamp component 2010 with, for example, a hinge.

Connecting a Bone Screw to the Clamp Components

The clamp components 2001 and/or 2010 can be configured to receive a screw (such as a bone screw) via a bone-screw aperture, guide, or hole 2181, as discussed further herein. The bone-screw hole 2181 may be positioned or manufactured to be located anywhere along the length of clamp component 2001 and/or 2010. The bone screw 2020 may be screwed, advanced, or inserted at least partially through the bone-screw hole 2181 and into bone, such as certain portions of the spine 2101.

The bone screw hole 2181 may an unthreaded hole, a threaded hole (which locks the relative position of the clamp arms), or may not even exist to allow the surgeon to "free-hand" the placement of the bone screw.

Figure 10A:
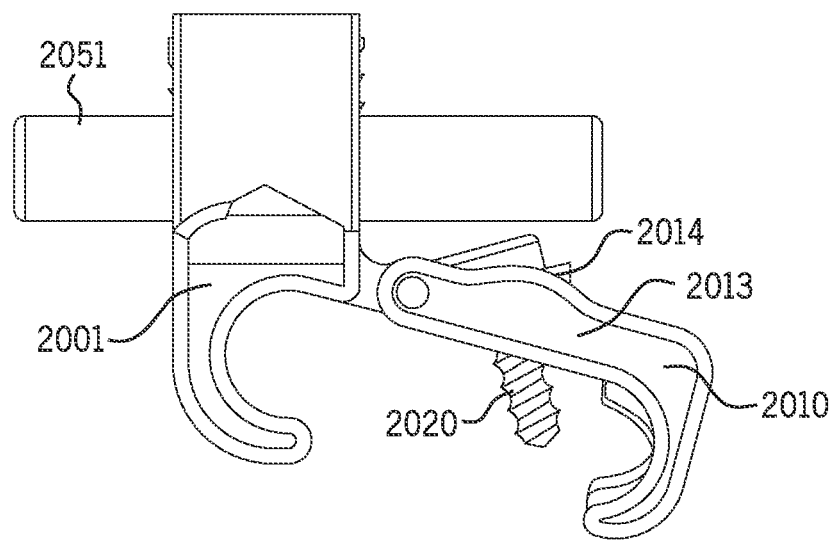
FIGS. 10A-10F provide a side, partially-sectional side, top end, sectional side, bottom end, and top views, respectively, of the screw-clamp apparatus of FIG. 5 engaged with a spacer, in accordance with an exemplary embodiment.
Figure 10B:
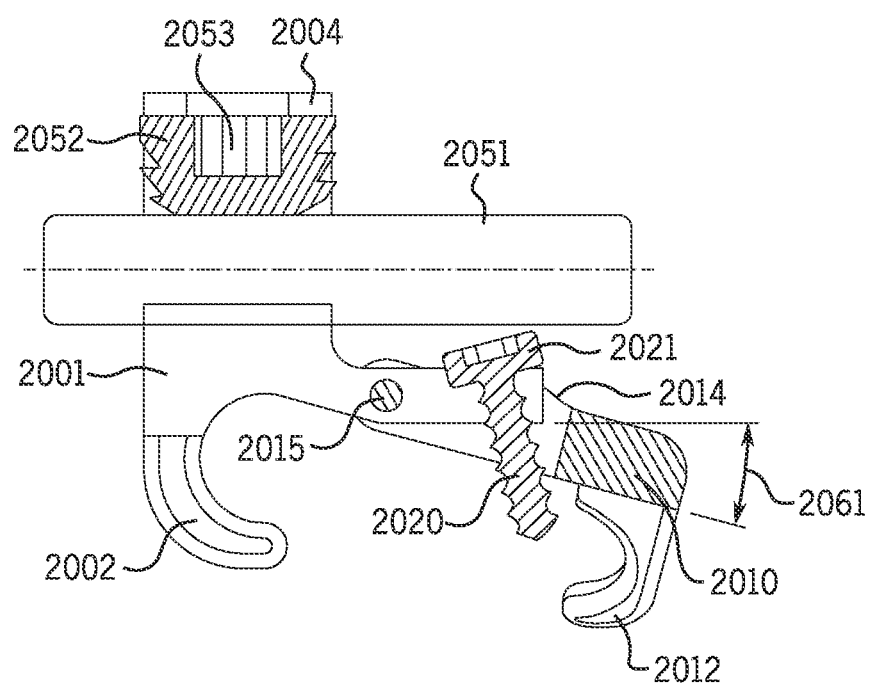
Figure 10C:
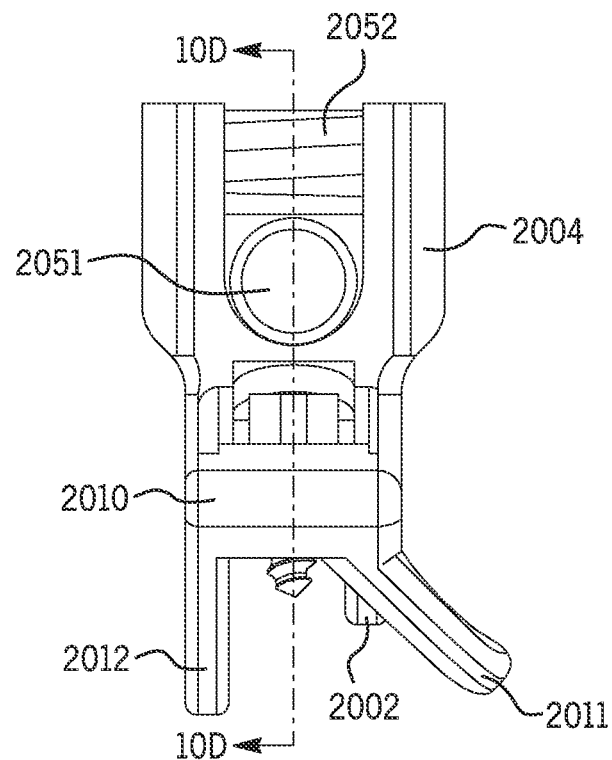
Figure 10D:
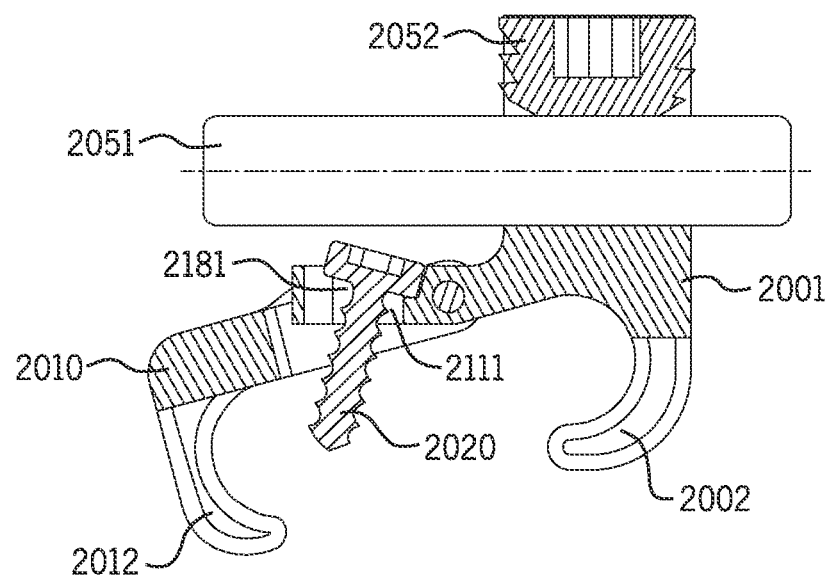
Figure 10E:
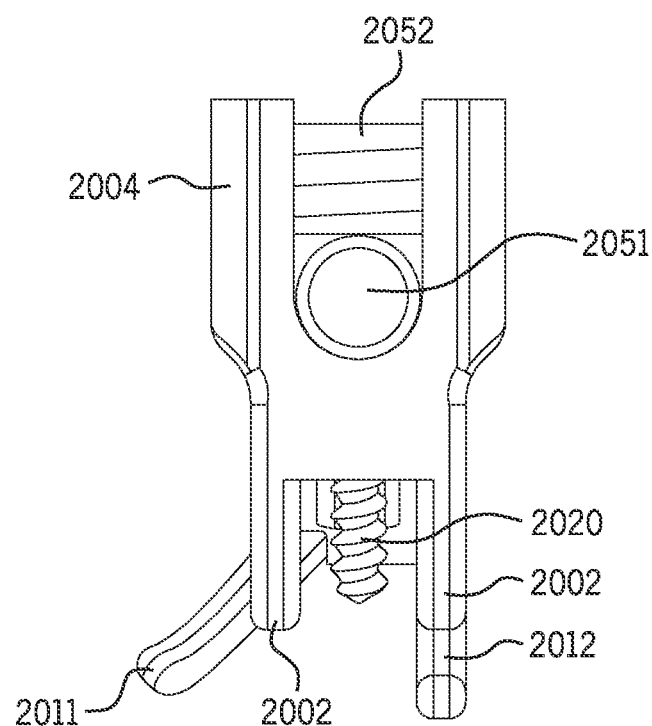
Figure 10F:
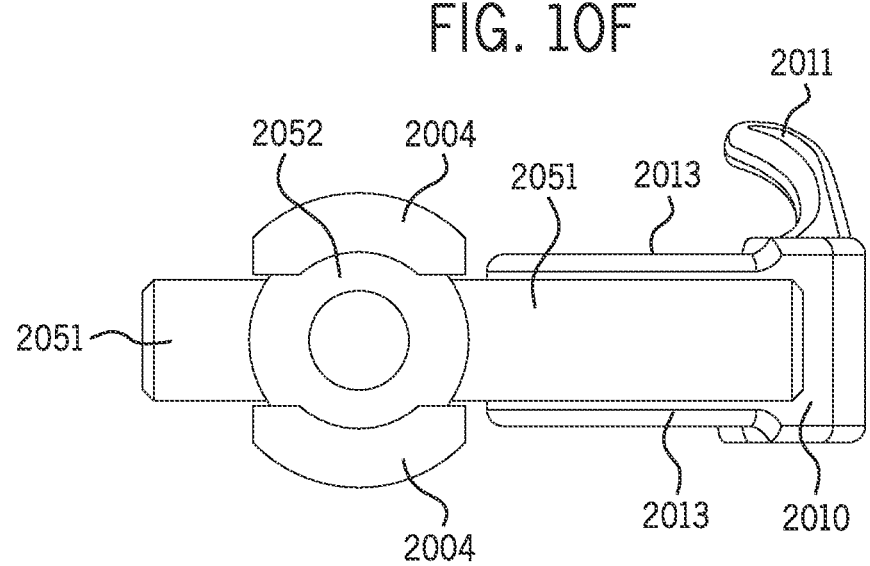

As shown in FIG. 10D, the bone screw hole 2181 may just be an unthreaded hole 2111 for receiving the screw 2020. This configuration allows for more freedom in the adjustment of the angular orientation of the screw 2020.

Figure 11:
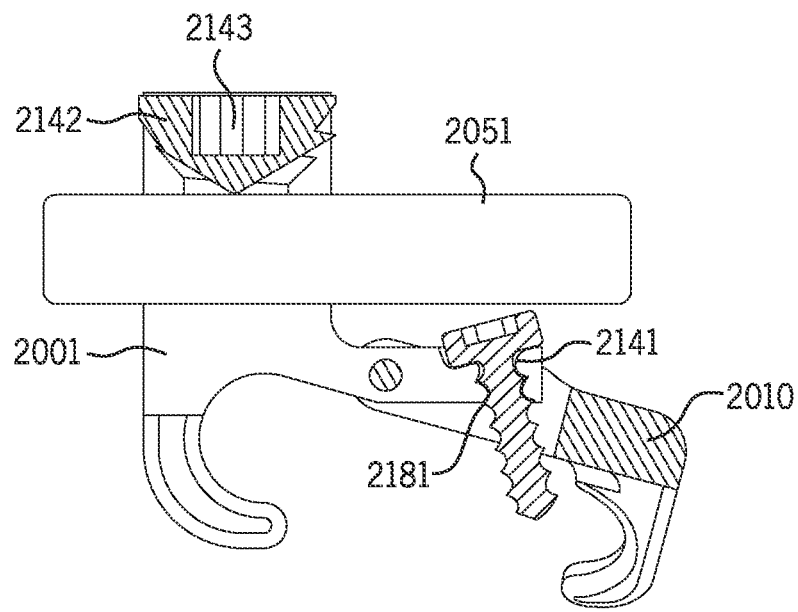
FIG. 11 illustrates a partially-sectional view of a screw-clamp apparatus including a bone-screw hole for a bone screw, in accordance with an exemplary embodiment.

Alternatively, as shown in FIG. 11, the bone screw hole 2181 may include a thread 2141 for engagement with bone screw 2020. This configuration can ensure the angular orientation of the screw 2020.

As yet another alternative, the bone-screw hole 2181 can include a guide or bushing 2182 for fitting therein. As shown in FIGS. 7A-7H, a c-clip 2183 can be provided to hold the bushing 2182 in place. FIGS. 7A and 7B provide a magnified, exploded view of bone-screw hole 2181, bushing 2182, and c-clip 2183. The c-clip 2183 may fit in groove 2184 on the outer aspect of bushing 2182 and a groove on the inner aspect of the bone-screw hole 2181 in arm 2003 of clamp component 2001. The grooves are slightly oversized relative to the c-clip 2183 so that bushing 2182 may rotate and tilt within bone-screw hole 2181 of arm 2003, which may allow the positioning and orientation of the screw 2020 within the bone-screw hole 2181 to be adjusted. As shown in FIG. 9, the bushing 2182 can alternatively or additionally have pins that assist in positioning the bushing 2182 in the bone-screw hole 2181. The bushing 2182 can allow the screw 2020 to tilt, rotate, pivot, or swivel relative to the bone-screw hole 2181 in the sagittal plane or in a polar fashion so that the screw 2020 is semi-constrained in its direction when inserted into bone. The bushing 2182 is illustrated as unthreaded, but may be threaded in some embodiments.

The positioning of the bone-screw hole 2181 and/or the bushing 2182 may determine the angle of the screw 2020 and accordingly may help properly orient the screw 2020 at a desired angle. For example, as illustrated in FIGS. 10B and 20A, the bone screw 2020 may be received into and secured at an angle relative to the arm 2003, including but not limited to an angle of 10 degrees (in either direction) with respect to arm 2003 in order to facilitate positioning of the clamp components 2001 and 2010 with respect to a bone disposed between hooks 2002 and hooks 2011, 2012 of clamp components 2001 and 2010, respectively. The bone screw hole 2181 may be configured to extend at least partially along the x-axis and the z-axis and may be angulated, for example at angle 2061 with respect to a plane of clamp component 2010 (in a proximal direction as demonstrated in FIG. 10B) to avoid neuroforamina. According to another embodiment shown in FIG. 21A, the bone screw 2020 may be inserted and secured perpendicularly into the arm 2003 of the clamp component 2001. Depending on the relative positioning and angling of the arms 2003 and 2013, the screw head 2021 of the bone screw 2020 may be angled with respect to the spacer 2051 (as shown in FIGS. 10B and 21A) or may be substantially parallel to, and optionally flush with, the spacer 2051 (as shown in FIG. 20A).

In a preferred embodiment, the bone-screw hole 2181 may be located at least partially within the arm 2003 of the first clamp component 2001 such that a bone screw 2020 may be inserted therein to engage with the second clamp component 2010 as the screw 2020 is tightened. As shown in FIGS. 6B-6D, 7A, and 9, the bone-screw hole 2181 may be located on the attachment end 2007 (e.g., the opposite end as the hooks 2002 (along the x-axis)). As shown in FIGS. 8A-8C, as the bone screw 2020 is tightened within or inserted into the bone-screw hole 2181, or advanced into underlying bone, the bone screw 2020 may cause the second clamp component 2010 to pivot toward the first clamp component 2001, thereby tightening the grip of the screw-clamp apparatus 2000 on the bones between the hooks 2002 and hooks 2011 and 2012.

Clamp arms 2013 of the second clamp component 2010 may include cam surfaces, a prominence, a protruding portion, or shoulders 2014 shaped and positioned to cause clamp component 2010 to rotate upon application of force (by, for example, the screw 2020) to cam surfaces 2014. The screw-clamp apparatus 2000 is configured such that a portion (such as the head) of screw 2020 may engage with a portion of the screw-clamp apparatus 2000. As demonstrated in FIGS. 6B, 8A, and 10B, screw head 2021 may abut a cam shoulder 2014 of clamp component 2010 as the screw 2020 is inserted or screwed into the screw hole 2181. As screw 2020 screws and/or advances into the screw hole 2181 and a bone, the head 2021 of screw 2020 may apply a force on a shoulder or cam surface 2014 of clamp arms 2013, causing the clamp components 2001 and 2010 to simultaneously close toward each other with respect to one another. In the illustrated embodiment, screw 2020 (or screw head 2021) abuts cam surface or shoulder 2014 on arm 2013 of asymmetric clamp component 2010, causing or forcing the clamp component 2010 to pivot or rotate toward the clamp component 2001 while the clamp component 2001 may remain stationary (with respect to the bone(s) the clamp component 2001 is at least partially secured around). In various embodiments, the cam surface 2014 may be disposed on the symmetrical clamp component 2001 and the screw hole 2181 may be disposed on the asymmetrical clamp component 2010.

Figure 13:
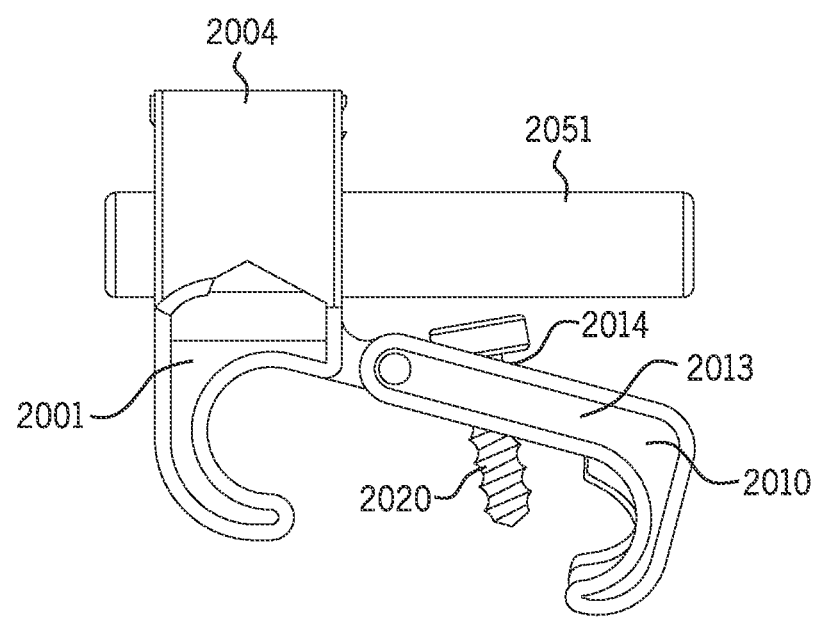
FIG. 13 illustrates a side view of a screw-clamp apparatus, in accordance with an exemplary embodiment.

As shown in FIGS. 10A and 13, the cam surfaces 2014 may be shaped according to the desired configuration. For example, the cam surfaces 2014 in FIG. 13 are substantially flat, while the cam surfaces 2014 in FIGS. 6A and 10A are at least partially rounded. The cam surfaces 2014 may engage with the head 2021 of the screw 2020. Alternatively or additionally, the head 2021 may be at least partially recessed within the clamp arms 2013 as shown in FIG. 10A.

FIGS. 8A-8C illustrate a screw-clamp apparatus 2000 in various positions related to transitioning from an open state to a closed state as the clamp components 2001 and 2010 pivot with respect to each other, in accordance with an exemplary inventive embodiment. FIG. 8A shows the screw-clamp apparatus 2000 in an open or extended position. The screw-clamp apparatus 2000 may be at least partially attached to a bone within the body while in the open position. According to one embodiment, the clamp component 2001 may be first attached to the bone before clamp component 2010. FIG. 8B shows the screw-clamp apparatus 2000 in a partially closed position, as clamp component 2010 rotates counterclockwise about pin 2015 with respect to clamp component 2001. The bone screw 2020 may help or cause the clamp component 2010 to pivot toward the clamp component 2010 by pressing on a surface of the clamp component 2010 as the screw 2020 is screwed into the bone-screw hole 2181 and into the bone. As discussed in more detail below, a spacer 2051 may be positioned and secured in the spacer-receiver 2004 of the clamp component 2001 as the screw-clamp apparatus 2000 is moved from the open position to the closed position. FIG. 8C shows the screw-clamp apparatus 2000 in a further closed position, as bone screw 2020 descends further into clamp component 2001 (and may be at least partially inserted into a bone), causing clamp component 2010 to rotate further counterclockwise (in the depicted orientation) and clamp around bone. As the screw-clamp apparatus 2000 moves from the open position to the closed position, the space between clamp components 2001 and 2010 (and their respective hooks) decreases, thereby increasing the amount of hold the screw-clamp apparatus 2000 has on the bone secured between the hooks.

As described previously, the screw 2020 may cause the clamp component 2010 to rotate with respect to the clamp component 2001. As screw 2020 is advanced downwardly, for example along its longitudinal axis 2022 (with respect to the length of the screw 2020, as shown in FIG. 6B), clamp component 2010 is forced to rotate clockwise about pin 2015 such that the space between hooks 2002 and hooks 2011, 2012 is decreased, thereby tightening the grip or hold that screw-clamp apparatus 2000 has on any bone disposed there between. The tightening provided allows the screw-clamp apparatus 2000 to act in a claw-like manner on a bone, independent of securing a spacer 2051 in the screw-clamp apparatus 2000. Additionally, if screw 2020 bottoms out, the securing and orientation of the spacer 2051 (that may be secured in the screw-clamp apparatus 2000) is not impacted.

Figure 12:
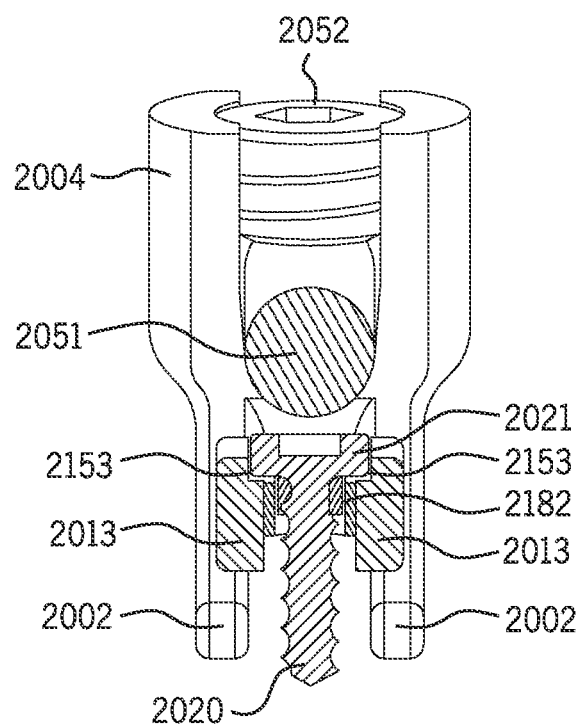
FIG. 12 illustrates a sectional, end view of a screw-clamp apparatus fitted with a bushing and including a recessed cam surface, in accordance with an exemplary embodiment.

In order for the bone screw 2020 to be fully engaged with the screw-clamp apparatus 2000 without preventing the spacer 2051 from being attached to the screw-clamp apparatus 2000, a portion of the clamp arm 2013 may be recessed to allow a screw head 2021 of the screw 2020 to at least partially recess within and at least partially abut an inner surface of the clamp arm 2013. For example, FIG. 12 illustrates a cam surface 2153 disposed in a recess within clamp arm 2013. FIG. 14 illustrates an exterior, side view of a screw-clamp apparatus 2000 with a recessed cam in accordance with an exemplary embodiment. Positioning cam surface 2153 on the inside of proximal clamp arm 2013 permits screw head 2021 to sit recessed within clamp arm 2013 and thereby have a lower profile to avoid interference with the spacer 2051. The radius of curvature of the cam surface 2153 may vary depending on the desired mechanical advantage. As shown in FIGS. 12 and 13, the cam surface 2153 may be at least partially hidden or concealed within the screw-clamp apparatus 2000.

As further alternatives, the bone-screw hole 2181 may be located on the clamp component attachment ends 2007 or 2017. Alternatively or additionally, the bone-screw hole 2181 may be located in the second clamp component 2010, such that the bone screw 2020 may be inserted therein to engage with the first clamp component 2001.

Spacer-Receivers of the Clamp Components

The first clamp component 2001 and/or the second clamp component 2010 may include a rod- or spacer-receiver 2004 (e.g., the "tulip" or u-shaped portion), which may be configured to secure or connect a spacer 2051 (FIG. 5) to the screw-clamp apparatus 2000. The spacer-receiver 2004 may optionally be positioned or located on the bone hook ends 2008 and/or 2018, atop or capping the clamp component 2001 and/or 2010. The spacer-receiver 2004 may be integrally formed as a part of clamp component 2001 or 2010.

As shown in FIGS. 10A-10F, the spacer-receiver 2004 may be positioned above arm 2003 or 2013, such that while the bone screw 2020 is engaged in arm 2003 or 2013, the bone screw 2020 may be positioned below a spacer or rod 2051 secured within the spacer-receiver 2004 (with the screw head 2021 above a portion of the clamp component 2001) in the engaged positioned (e.g., in the closed position), thereby preventing bone screw 2020 from backing out of the bone, dislodging, displacing, loosening, retracting out of the bone or the screw-clamp apparatus 2000, becoming lost within the body, and detaching the screw-clamp apparatus 2000 from the bone.

As depicted in FIG. 9, the spacer-receiver 2004 may be structured to receive the spacer 2051 and a retaining member, engagement member, spacer-securing component, set screw, or spacer-securing component 2052 for securing the spacer 2051 in the spacer-receiver 2004 of clamp component 2001. Accordingly, the spacer-receiver 2004 may include a plurality of threads 2005 and a base 2006 disposed at a distance above the inner lowest surface or platform of the u-shaped spacer-receiver. The spacer-securing component 2052 may be screwed, attached, or secured within the spacer-receiver 2004 (on top of the spacer 2051) and may be removably engagable with the spacer-receiver 2004. The spacer-securing component 2052 may include a keyed recess 2053 shaped to receive a tool, such as an hex key, for applying torque to the spacer-securing component 2052 for engagement with the spacer-receiver 2004.

As shown in FIGS. 10B and 10D, the spacer-securing component 2052 is depicted as having a planar bottom surface for engaging the spacer 2051. However, the spacer-securing component 2052 may include other geometries in accordance with inventive embodiments disclosed herein. For example, FIG. 11 depicts an alternative engagement spacer-securing component 2142, which may be comparable to the spacer-securing component 2052. As demonstrated in FIG. 11, the engagement spacer-securing component 2142, configured for engaging and securing the spacer 2051, may have alternative geometries such as a pointed base and, like the spacer-securing component 2052, the spacer-securing component 2142 may include a keyed recess 2143 shaped to receive a tool for applying torque to spacer-securing component 2142 for engagement with the spacer-receiver 2004.

The spacer-securing component 2052 may be screwed into the threads 2005 of the spacer-receiver 2004 over the spacer 2051 to securely maintain the spacer 2051 within the u-shaped channel of the spacer-receiver 2004, such that the spacer 2051 is positioned between the clamp component 2001 and the spacer-securing component 2052, as shown in FIGS. 10B-10E. As shown in FIGS. 10A-10F, the spacer 2051 may be secured along the longitudinal axis of the screw-clamp apparatus 2000, above the screw 2020, within the spacer-receiver 2004, and below the spacer-securing component 2052.

At least one other screw-clamp apparatus 2000 may also attach to the spacer 2051, such that the multiple screw-clamp apparatus 2000 are aligned and connected with each other along a length of the spacer 2051 and/or a spine, as shown in FIG. 5. Alternatively or additionally, the spacer-receiver 2004 may allow the screw-clamp apparatus 2000 to connect to multiple other devices such as conventional hooks or pedicle screws.

According to one embodiment as shown in FIGS. 20A-20E, 21A-21E, 22A-22D, and 23A-23E, both clamp components 2001 and 2010 may include a spacer-receiver 2004 such that there are dual or two spacer-receivers 2004 on the screw-clamp apparatus 2000 to further secure and strongly hold the spacer 2051 (e.g., a first spacer-receiver 2004 may be located on the first clamp component 2001 and a second spacer-receiver 2004 may be located on the second clamp component 2010).

The connecting rod or spacer 2051 may be designed according to the desired configuration and the spacer-receiver 2004 may be designed to accept and secure a variety of different spacers 2051. For example, the spacer 2051 may be stiff or rigid. Alternatively or additionally, the spacer 2051 (or portions of the spacer 2051) may be non-rigid. This may give the patient using the screw-clamp apparatus a greater number of degrees of freedom to move their spine while providing sufficient support to the spine 2101. Alternatively or additionally, the spacer 2051 (or portions of the spacer 2051) may be expandable. The spacer 2051 may further be shaped according to the desired configuration. For example, a curved or straight spacer 2051 may be used, depending on the desired configuration.

Length-Adjusting Mechanisms

The screw-clamp apparatus 2000 may further utilize a variety of different mechanisms to move or adjust the components of the screw-clamp apparatus 2000. The size of various components within the screw-clamp apparatus 2000 (and the overall length of the screw-clamp apparatus 2000) may be configured to be adjustable. For example, the screw-clamp apparatus 2000 may include a length-adjusting mechanism that is configured to adjust a longitudinal length of the screw-clamp apparatus 2000. Accordingly, the length-adjusting mechanism may allow the screw-clamp apparatus 2000 to compress, elongate, or secure the spine 2101 or fit with a variety of different spine sizes.

For example, according to one embodiment as shown in FIG. 15, the length of the clamp components 2001 and 2010 may be adjusted along the longitudinal direction of the screw-clamp apparatus 2000 with a threaded engagement between the first attachment end 2007 and the first hook end 2008. For example, the threaded engagement may include a threaded rod 2230 movable at least partially within a shaft 2232. Relative rotation of the threaded engagement may adjust the longitudinal length of the screw-clamp apparatus 2000 by elongating or shortening the clamp component 2001. The shaft 2232 may be threaded and a nut 2234 may optionally be included to secure the threaded rod 2230 in position within the shaft 2232. The threaded rod 2230 and the shaft 2232 may be located on either the arm 2003 of the first attachment end 2007 or on the body of the clamp component 2001 (e.g., the first hook end 2008). The threaded engagement may alternatively or additionally be located on the clamp component 2010 to adjust the length of the arm 2013 relative to the body of the clamp component 2010 (thereby adjusting the length of the clamp component 2010 and the entire screw-clamp apparatus 2000).

According to another embodiment, the length-adjusting mechanism may allow the lengths and the angles of the arms 2003 and 2013 to be adjustable with respect to the clamp components 2001 and 2010. For example, as shown in FIGS. 16A-16D and 17A-17E, a projection, such as the arm 2003, may move, pivot, and/or slide at least partially within, along, or through a shaft, slot, groove, or complementary recess 2242 in the clamp component 2001. Adjusting the positioning of the arm 2003 relative to the clamp component 2001 may also adjust the configuration and length of the entire screw-clamp apparatus 2000, as well as the relative positioning between the clamp components 2001 and 2010. Once the screw-clamp apparatus 2000 is fully assembled, the projection is fully secured within the complementary recess 2242. The projection and the complementary recess may be located on either the first attachment end 2007 or the first hook end 2008. Alternatively or additionally, the complementary recess 2242 may be located on the second clamp component 2010 that a projection, such as the arm 2013, may be adjusted within.

The recess 2242 may be shaped to complement the shape of the arm 2003. The recess 2242 may be a dovetail shaft or have a trapezoidal shape, as shown in FIGS. 16D, 17B, 17C, and 18. For example, both the projection and the recess 2242 may be tapered in a complementary manner to form a dovetail connection. However, it is anticipated that the recess 2242 (as well as the arm 2003) may have a variety of different shapes according to the desired use and configuration including, but not limited to rectangular, oval, round, triangular, pentagonal, and hexagonal.

Figure 16A:
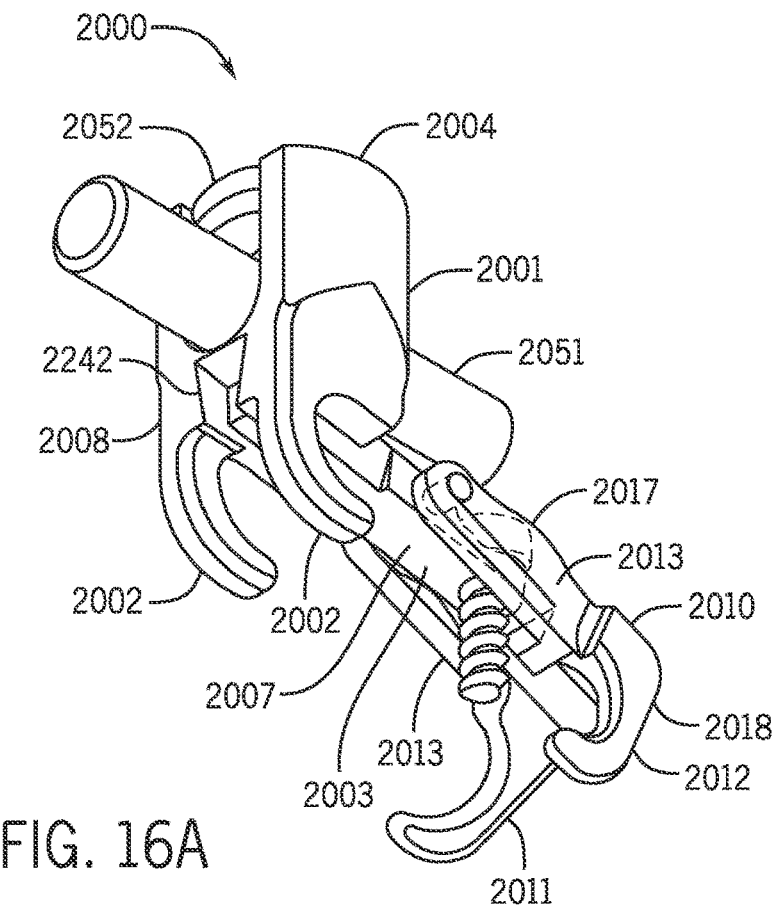
FIGS. 16A-16D illustrate a perspective view, a side view, an end view, and a partially cross-sectional view (through Section 16D of FIG. 16C), respectively of a screw-clamp apparatus according to one embodiment.
Figure 16B:
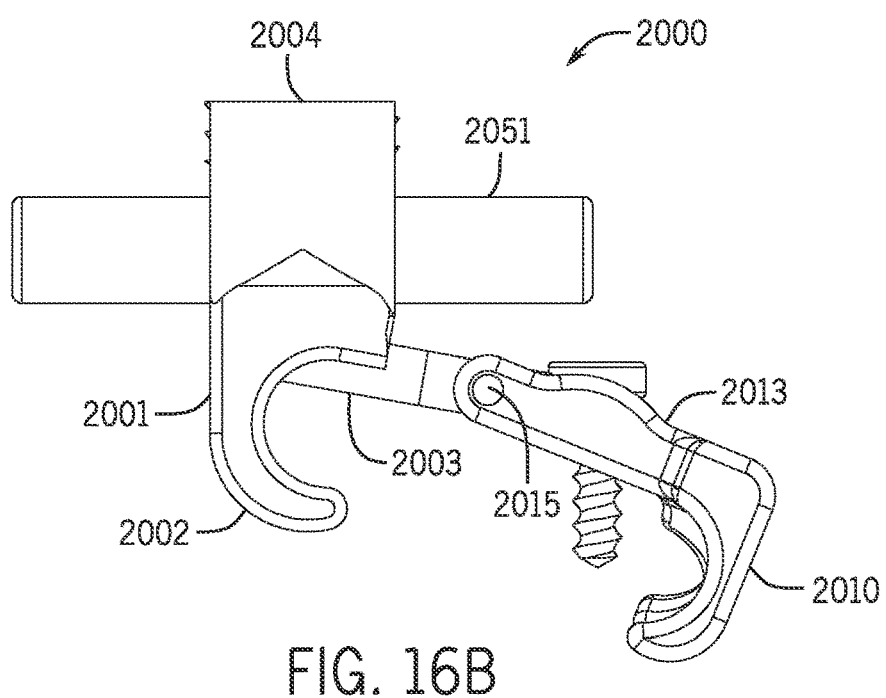
Figure 16C:
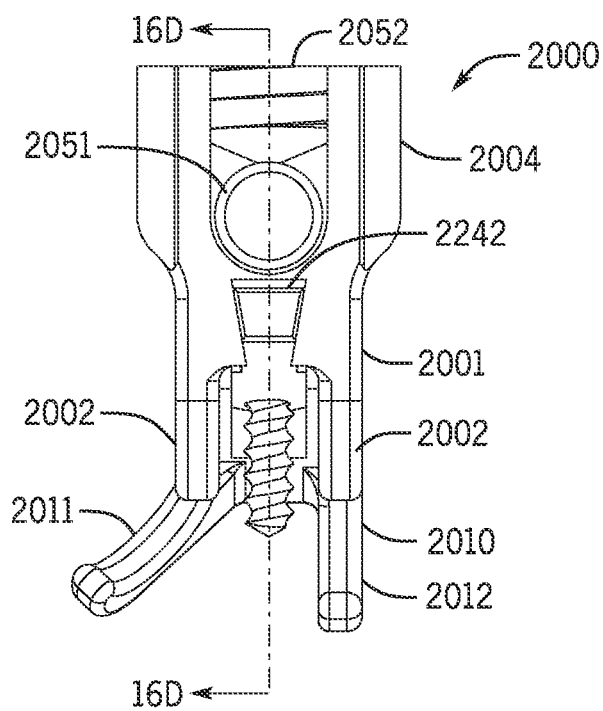
Figure 16D:
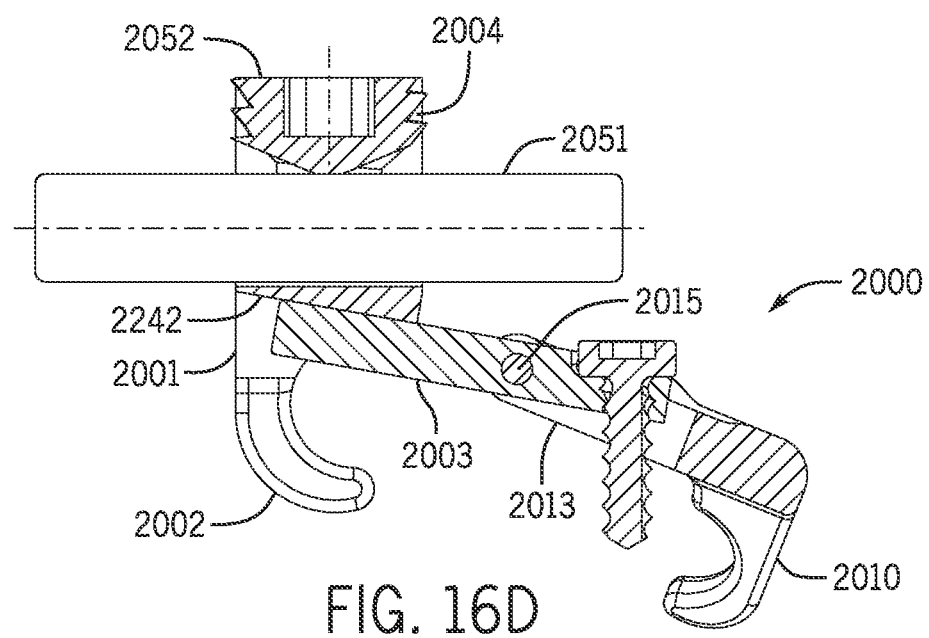
Figure 17A:
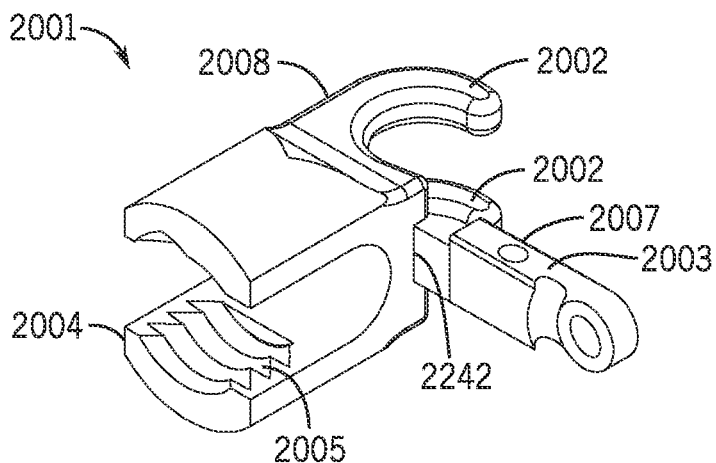
FIGS. 17A-17E illustrate perspective view, perspective end-view, end view, top view, and a cross-sectional view (through Section 17E of FIG. 17D), respectively, of the clamp component and arm that may be disposed within the screw-clamp apparatus of FIG. 16A.
Figure 17B:
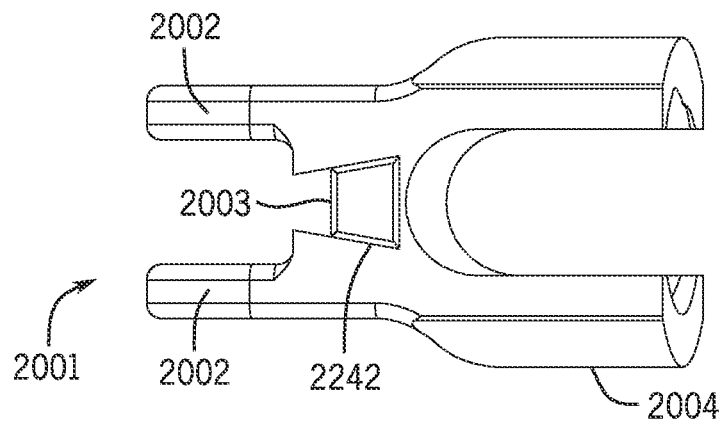
Figure 17C:
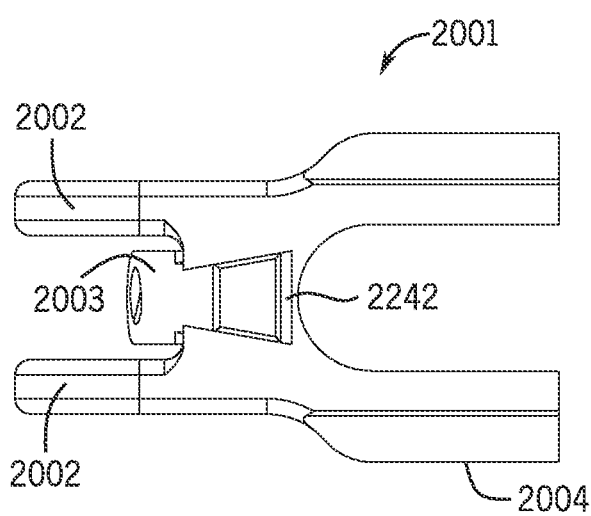
Figure 17D:
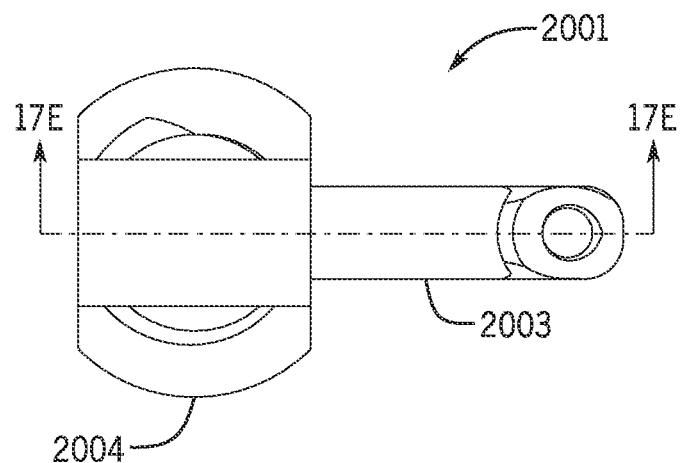
Figure 17E:
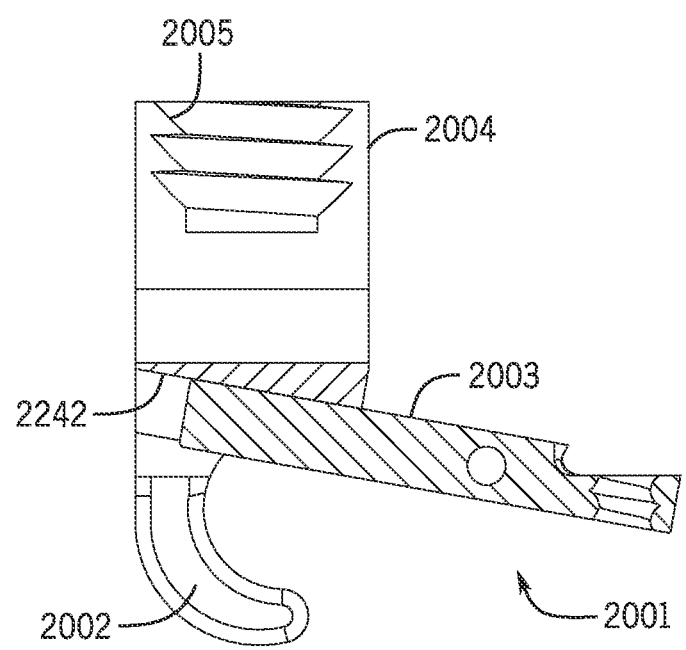

According to one embodiment, the recess 2242 may be shaped to maintain a consistent angle of the arm 2003 with respect to the clamp component 2001 as the arm 2003 is moved through the recess 2242. As shown in FIGS. 16D and 17E, the recess 2242 may extend longitudinally (or at an angle) through the length of the clamp component 2001.

Figure 18:
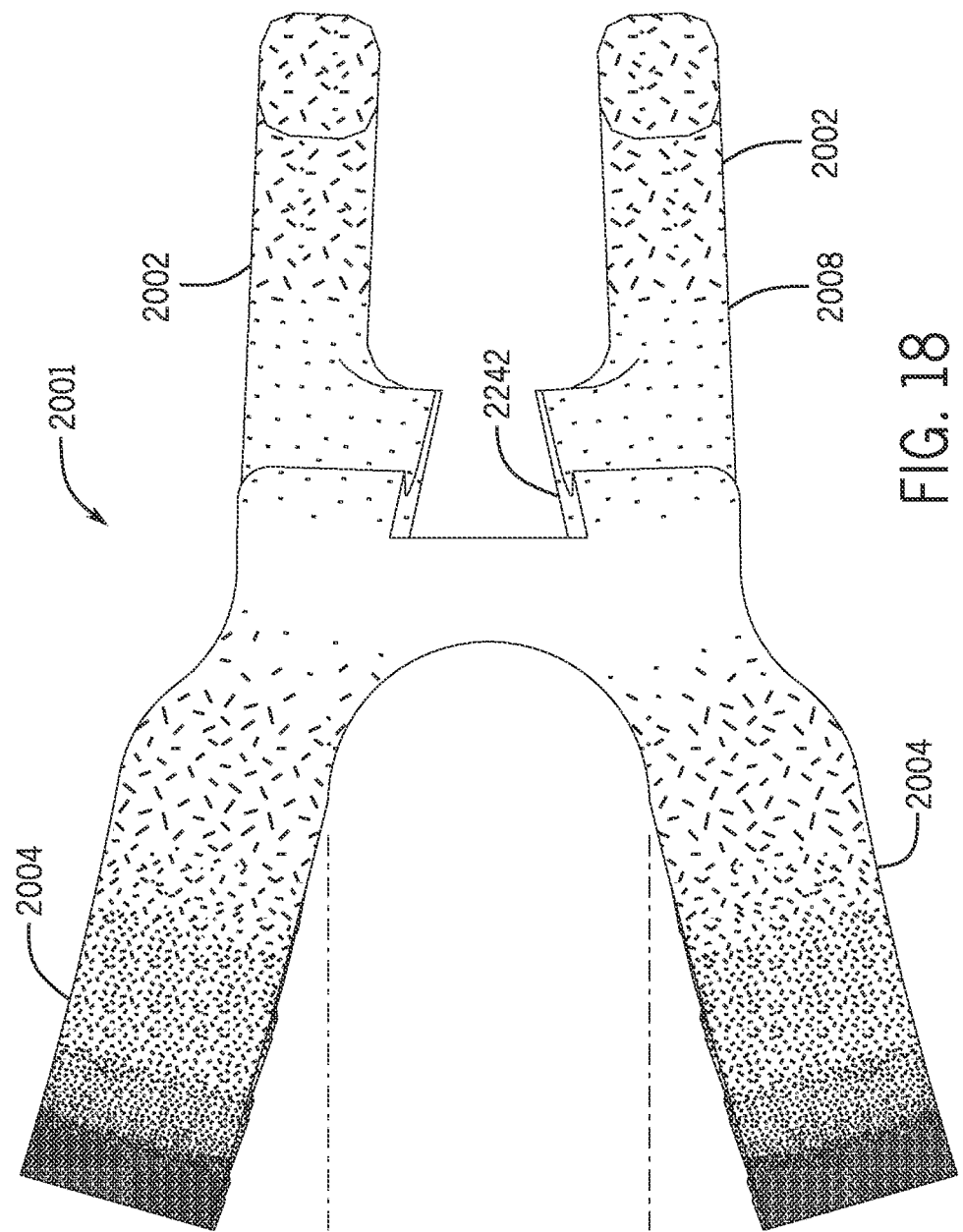
FIG. 18 illustrates a front view of the clamp component of FIG. 16A with the spacer-receiver in an expanded or deflected position. where a greater density of stippling indicates greater deflection.

According to another embodiment, the recess 2242 may be configured to allow the angle of the arm 2003 to be altered relative to the clamp component 2001 before the arm 2003 is fully secured within the recess 2242. For example, at least a portion of the recess 2242 (such as the sides of the first hook end 2008) may be at least partially flexible (e.g., expandable and/or contractible) and may move as a result of the relative geometry of other portions of the clamp component 2001, thus allowing the angle and the longitudinal position of the arm 2003 to be adjusted and further securing and/or locking the arm 2003 into place within the recess 2242. For example, before the spacer-securing component 2052 is fully attached to the spacer-receiver 2004, the arm 2003 may move and be adjusted within the recess 2242 to obtain the optimal relative positioning. As the spacer-securing component 2052 is attached, moved, tightened, or screwed further into place in the spacer-receiver 2004, the sides of the spacer-receiver 2004 may at least partially splay, spread, deflect, expand, or bend outward, as shown in FIG. 18. (FIG. 18 depicts the side of the spacer-receiver 2004 deflecting outward under 100 N of force. However, it is anticipated that the sides of the spacer-receiver 2004 may be more or less flexible according to the desired use.) The movement of the spacer-receiver 2004 may secondarily cause the sides of the recess 2242 to narrow move inward and at least partially close, thereby compressing, securing, pinching, and/or locking the arm 2003 within the recess 2242, which holds or maintains the position of the arm 2003 within the recess 2242.

In an alternative embodiment, the clamp components 2001 and 2010 may be adjusted relative to each other due to an interaction or interlocking mechanism between the arm 2003 and 2013. For example, as shown in FIGS. 19A-23E, the first attachment end 2007 of the first clamp component 2001 may have two arms 2003, which may fit or extend at least partially within two arms 2013 of the second attachment end 2017 of the second clamp component 2010 to adjustably attach the first clamp component 2001 and the second clamp component 2010. The arms 2003 may fit within, slide or move between and in and out of, and secure to the arms 2013 to adjust the positioning and length of the screw-clamp apparatus 2000. For example, the arms 2003 may be pulled at least partially out of the arms 2013 to elongate or extend the screw-clamp apparatus 2000 (and the distance between the clamp components 2001 and 2010). Due to an outward force or pressure in the lateral direction that the arms 2003 may exert along an inside region of the arms 2013 (and/or an inward force or pressure the arms 2013 may exert along an outside region of the arms 2003), the arms 2003 and 2013 may lock or secure together. Alternatively or additionally, it is anticipated that the arms 2013 may fit at least partially within the arms 2003. It is further anticipated that the interlocking mechanism may at least partially be within at least one of the hook ends 2008 and 2018 instead of (or in addition to) the attachment ends 2007 and 2017.

As shown in FIGS. 19A-19F, the arm 2003 may slide at least partially smoothly within the arms 2013 and may be positioned and secured anywhere along the length of the arms 2013 and/or the clamp component 2010 due to the outward force and the resulting friction of the arms 2003 against the arms 2013. A portion of the arms 2003 and 2013 may have a frictional surface or coating to provide greater traction between the arms 2003 and 2013 to maintain the relative position.

According to one embodiment, the bone screw 2020 may push the arms 2003 outward toward the arms 2013, which secures or compresses the arms 2003 and 2013 together. For example, as shown in FIGS. 19A, 19C, 19F, 20A, 20C, 20F, 21A, 21C, and 21F, the bone-screw hole 2181 may be positioned between the arms 2003, such that inserting the bone screw 2020 through the bone-screw hole 2181 and forces the arms 2003 outward (e.g., away from the longitudinal midline of the screw-clamp apparatus 2000) toward the arms 2013, thus engaging the arms 2003 and 2013.

Alternatively or additionally, additional components or mechanisms, such as step or ratcheting mechanisms, may be provided between the arms 2003 and 2013 to securely hold the clamp components 2001 and 2010 together. A variety of different ratcheting mechanisms may be used to adjust and maintain the relative positioning between the clamp components 2001 and 2010, according to the desired configuration and use, as shown, for example, in FIGS. 20A-20F, 21A-21F, 22A-22D, and 23A-23E. The ratcheting mechanism may allow the clamp components 2001 and 2010 to move in step-wise increments away from or towards each other. For example, the arm 2003 may have notches or projections 2254 extending or protruding from an outer surface or portion that may at least partially fit within and interlock with holes, grooves, or indentations 2256 along an inside surface or region of the arms 2013. The projections 2254 may lock into any of the indentations 2256 to securely lock and hold the clamp components 2001 and 2010 together in a particular position.

The projections 2254 and indentations 2256 may be shaped according to the desired configuration. For example, the projections 2254 may be rectangular, as shown in FIGS. 20A-20F and 21A-21F. As shown in FIGS. 22A-22D, 23A-23E, and 24, the relative geometry of the projections 2254 and the indentations 2256 may cause the arms 2003 (and the projections 2254) to move preferentially in one direction relative to the arms 2013 (along the indentations 2256). For example, the substantially triangular shape of the projections 2254 may allow the arms 2003 to easily move toward the clamp component 2010, but may prevent the arms 2003 from dislodging and moving away from the clamp component 2010. However, it is anticipated that the projections 2254 and indentations 2256 may have any shape and may be at least partially complementary to each other.

The arms 2003 and 2013 may have any number of projections 2254 and indentations 2256. For example, as shown in the figures, the arms 2003 may each have a projection 2254 and the arms 2013 may each have three indentations 2256. It is further anticipated that the projections 2254 may be located along the arms 2013 and the indentations 2256 may be located along the arms 2003.

Figure 24:
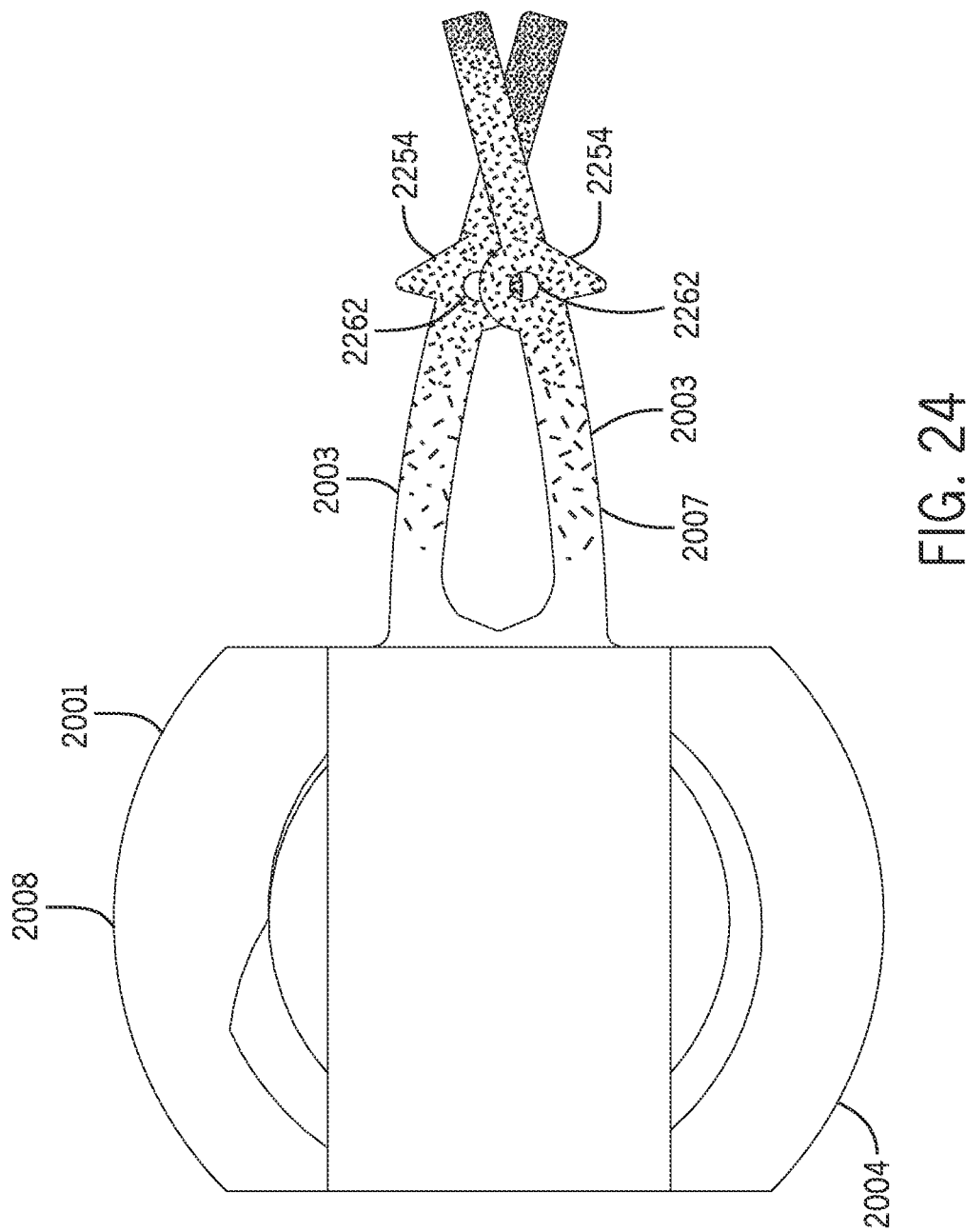
FIG. 24 illustrates a top view of a clamp component that may be disposed within the screw-clamp apparatus of FIG. 22A with the arms in a deflected position, where a greater density of stippling indicates greater deflection.

Optionally, the arms 2003 may include at least one ratchet release aperture, pinhole, or hole 2262 and the arms 2003 may be at least partially flexible. The release holes 2262 may be positioned or manufactured to be located anywhere along the arms 2003 or 2013. According to one embodiment, the release holes 2262 may be located near or on the projections 2254. The release holes 2262 may be extend at least partially through the arms 2003 or 2013 and may correspond with or complement the shape of a tool. The surgeon may use the tool to at least partially attach with or fix to the release holes 2262 to bend the arms 2003 (or 2013) inward together by moving the release holes 2262 on each arm 2003 toward each other, as shown in FIG. 24. By bending the arms 2003, the projections 2254 may be released from the indentations 2256 and may allow the clamp components 2001 and 2010 to be adjusted or move relative to each other.

As shown in FIG. 24, the arms 2003 with the projections 2254 may be at least partially flexible in order to fit within the arms 2013. For example, the arms 2003 may flex, deflect, or bend inward to allow the arms 2003 and 2013 to move relative to each other. FIG. 24 depicts the arms 2003 deflecting inward under 15 LBf, which may be applied through a tool attached to at least one of the release holes 2262. However, it is anticipated that the arms 2003 may be more or less flexible than those shown in FIG. 24. Once the arms 2003 and 2013 are properly positioned with respect to each other, the arms 2003 may move outward to lock or secure the projections 2254 within the indentations 2256 of the arms 2013, thereby securing the clamp components 2001 and 2010 together.

Additional Benefits and Embodiments of the Screw-Clamp Apparatus 2000

The bilateral constructs of the screw-clamp apparatus 2000, which are commonly applied during the correction of a scoliotic spine, may allow for powerful derotation maneuvers by providing a surgeon with greater leverage to perform axial rotation maneuvers via device holders or extensions that are temporarily held onto the devices acting as lever arms. For example, the bilateral constructs extend up (perpendicular) to the spinal axis and allow a surgeon to twist the spine about its long axis. In a manner similar to older hooks, the embodiments of the screw-clamp apparatus 2000 disclosed herein may be placed under direct visualization. This contrasts with pedicle screws that require imaging at some point to assure the surgeon they are correctly placed. Unlike conventional pedicle screws, screws 2020 used with the embodiments disclosed herein (i.e., bone screw 2020) are small enough so that there is substantially no danger to the nervous structure and thus visualization of bone screw 2020 into the bone is not required.

The screw-clamp apparatus 2000 may further allow clamp component 2001 to be first be positioned within the body (at least partially around a bone with the hooks 2002) and then the other clamp component 2001 to be subsequently pivoted and positioned within the body (at least partially around a bone with the hooks 2011, 2012). Positioning one clamp component at a time (in series, instead of in parallel at the same time) may allow the screw-clamp apparatus 2000 to be attached and positioned easier. Further, it may be easier for the bone screw 2020 to be accurately and precisely positioned within the bone since the clamp component 2001 has already been secured and properly positioned with the bone (instead of clamping both clamp components 2001 and 2010 while screwing in the bone screw 2020). Additionally, since the clamp component 2001 may remain stationary and upright around the bone as the clamp component 2010 is pivoted, the spacer 2051 may be more securely held in the spacer-receiver 2004 since the spacer-receiver 2004 is not tilted.

Screw-clamp apparatuses and components described herein may be composed of a material that is biocompatible and/or include a biocompatible coating on the attachment components to enhance fixation of the attachment members to bone comprised of a porous surface texture. The biocompatible coating/material can comprise, for example, hydroxyappetite. The screw-clamp apparatus embodiments may be made of different materials such that, for example, the material forming the bone screw is different than the material forming the clamp components and/or the material. In various embodiments, the screw-clamp apparatus in accordance with various inventive embodiments may be composed of materials such as, titanium, cobalt, and chrome-alloy, and stainless steel.

As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of the screw-clamp or components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, describes techniques, or the like, this application controls.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. A screw-clamp apparatus comprising:
   a first clamp component comprising a first attachment end and at least one hook on a first hook end;
   a second clamp component comprising a second attachment end and at least one hook on a second hook end,
   wherein the first attachment end and the second attachment end are configured to attach the first clamp component and the second clamp component together, wherein the first clamp component and the second clamp component are pivotable relative to each other when the first clamp component and the second clamp component are attached together;
   a screw hole located in one of the first clamp component and the second clamp component;
   a screw configured to be inserted through the screw hole and to be inserted into bone;
   a first spacer-receiver located on one of the first clamp component and the second clamp component, wherein the first spacer-receiver is configured to secure a spacer; and
   wherein a longitudinal length of the screw-clamp apparatus is adjustable such that a distance between the first clamp component and the second clamp component is adjustable,
   wherein the second attachment end includes two clamp arms that are configured to receive at least a portion of the first attachment end therebetween,
   wherein the screw hole is located in the first attachment end of the first clamp component such that at least a portion of the screw is positioned between the two clamp arms when the first clamp component and the second clamp component are attached together.

2. The screw-clamp apparatus of claim 1, further comprising a threaded engagement between the first attachment end and the first hook end, wherein the longitudinal length of the screw-clamp apparatus is adjusted by relative rotation of the threaded engagement.

3. The screw-clamp apparatus of claim 1, further comprising a length-adjusting mechanism that is configured to adjust the longitudinal length of the screw-clamp apparatus, wherein the length-adjusting mechanism includes a projection on one of the first attachment end and the first hook end and a complementary recess on the other of the first attachment end and the first hook end, wherein the projection is movable and securable within the recess.

4. The screw-clamp apparatus of claim 3, wherein the length-adjusting mechanism is a dovetail connection and the projection is tapered.

5. The screw-clamp apparatus of claim 3, wherein the first hook end is at least partially flexible such that attaching a spacer-securing component into the first spacer-receiver narrows the recess and secures the projection within the recess, wherein the first spacer-receiver is located on the first clamp component.

6. The screw-clamp apparatus of claim 1, further comprising a length-adjusting mechanism that is configured to adjust the longitudinal length of the screw-clamp apparatus, wherein the length-adjusting mechanism includes a projection and a complementary recess, wherein the projection is movable and securable within the recess.

* * * * *